(12) United States Patent
Hill et al.

(10) Patent No.: US 8,592,557 B2
(45) Date of Patent: *Nov. 26, 2013

(54) MULTIMERIC TNF RECEPTOR FUSION PROTEINS AND NUCLEIC ACIDS ENCODING SAME

(75) Inventors: Oliver Hill, Neckarsteinach (DE); Christian Gieffers, Dossenheim (DE); Carmen Fischer, Sinsheim-Dühren (DE)

(73) Assignee: Apogenix GmbH, Heidelberg (DE)

( * ) Notice: Subject to any disclaimer, the term of this patent is extended or adjusted under 35 U.S.C. 154(b) by 0 days.

This patent is subject to a terminal disclaimer.

(21) Appl. No.: 12/999,607

(22) PCT Filed: Jun. 15, 2009

(86) PCT No.: PCT/EP2009/057396
§ 371 (c)(1),
(2), (4) Date: Jan. 24, 2011

(87) PCT Pub. No.: WO2010/003766
PCT Pub. Date: Jan. 14, 2010

(65) Prior Publication Data
US 2011/0111494 A1    May 12, 2011

(30) Foreign Application Priority Data

Jun. 17, 2008  (EP) .................................... 08010978

(51) Int. Cl.
| C07K 1/00 | (2006.01) |
| C07K 14/00 | (2006.01) |
| C07K 17/00 | (2006.01) |
| C12P 21/06 | (2006.01) |
| C12N 1/20 | (2006.01) |
| C12N 15/00 | (2006.01) |
| C12N 5/00 | (2006.01) |
| C12N 5/02 | (2006.01) |
| C12N 15/74 | (2006.01) |
| C07H 21/00 | (2006.01) |

(52) U.S. Cl.
USPC .... 530/350; 435/69.1; 435/252.3; 435/320.1; 435/325; 435/471; 536/23.5

(58) Field of Classification Search
None
See application file for complete search history.

(56) References Cited

U.S. PATENT DOCUMENTS

| 5,874,546 A * | 2/1999 | Nagata et al. ................. 530/395 |
| 6,608,044 B1 * | 8/2003 | Aderka et al. ................. 514/56 |
| 2004/0047873 A1 | 3/2004 | Al-Shamkhani et al. |
| 2010/0199364 A1 | 8/2010 | Hill et al. |
| 2012/0041181 A1 | 2/2012 | Hill et al. |

FOREIGN PATENT DOCUMENTS

| WO | WO-01/42298 | 6/2001 |
| WO | WO-02/00893 | 1/2002 |
| WO | WO-02/090553 | 11/2002 |
| WO | WO-2004/033486 | 4/2004 |

OTHER PUBLICATIONS

Herbein G, et al. Proc. Soc. Exp. Biol. Med. 223:241-257, 2000 (only pp. 241-243 provided herewith).*
Guoqing C, et al. Science, 296(5573):1634-1635, May 31, 2002.*
International Search Report mailed Aug. 3, 2010 for PCT/EP2009/057396.
Meier et al.: "Foldon, The Natural Trimerization Domain of T4 Fibritin, Dissociates into a Monomeric A-state Form containing a Stable beta-Hairpin: Atomic Details of Trimer Dissociation and Local beta-Hairpin Stability from Residual Dipolar Couplings". Journal of Molecular Biology, London, GB, vol. 344, No. 4, Dec 3, 2004, pp. 1051-1069.
Haakansson et al.: Collectin Structure: a review. Protein Science, Cambridge University Press, Cambridge, GB, vol. 9, No. 9, Sep. 1, 2000, pp. 1607-1617.
Wajant: "Death Receptors". Essays in Biochemistry, Portland Press, Colchester, GB, vol. 39, Jan. 1, 2003, pp. 53-71.

* cited by examiner

*Primary Examiner* — Robert Landsman
(74) *Attorney, Agent, or Firm* — Perkins Coie LLP; Viola T. Kung

(57) ABSTRACT

The present invention refers to fusion proteins comprising a TNF receptor family extracellular domain fused to a trimerization domain, and a nucleic acid molecule encoding the fusion protein. The fusion protein may be present as a trimeric complex. It is suitable for therapeutic, diagnostic and/or research applications.

22 Claims, 9 Drawing Sheets

Figure 1:
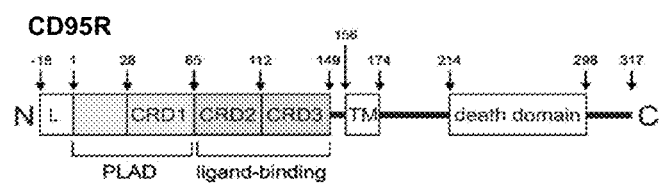

Covalent crosslinking of the trimeric CD95R-fusionsproteins with BS³

Covalent crosslinking of the dimeric CD95R-fusionsprotein with BS³

D

Figure 6A

TNFR superfamily

| receptor | aliases | reference-sequence[a] | LBD definition[b] |
|---|---|---|---|
| TNFRSF1a | CD120a, FPF, MGC19588, TBP1, TNF-R, TNF-R-I, TNF-R55, TNFAR, TNFR1, TNFR55, TNFR60, p55, p55-R, p60 | ACCESSION NP_001056<br>VERSION NP_001056.1 | Leu30 – Gly209<br>Leu30 – Gly204<br>Leu30 – Glu200 |
| TNFRSF1b | CD120b, TBPII, TNF-R-II, TNF-R75, TNFBR, TNFR2, TNFR80, p75, p75TNFR | ACCESSION NP_001057<br>VERSION NP_001057.1 | Leu23 – Gly253<br>Leu23 – Gly257<br>Leu23 - Ser204 |
| TNFRSF3 | CD18, D12S370, LT-BETA-R, TNF-R-III, TNFCR, TNFR-RP, TNFR2-RP, LTBR | ACCESSION NP_002333<br>VERSION NP_002333.1 | Ser28 - Gly223<br>Ser28 – Thr224 |
| TNFRSF4 | ACT35, CD134, OX40, TXGP1L | ACCESSION NP_003318<br>VERSION NP_003318.1 | Leu29 – Asp170<br>Leu29 – Gly211 |
| TNFRSF5 | Bp50, CDW40, MGC9013, p50, CD40 | ACCESSION NP_001241<br>VERSION NP_001241.1 | Glu21 – Arg191 |
| TNFRSF6 | ALPS1A, APO-1, APT1, CD95, FAS1, FASTM, FAS | ACCESSION NP_000034<br>VERSION NP_000034.1 | Arg17 – Glu168 |
| TNFRSF6b | DCR3, DJ583P15.1.1, M68, TR6 | ACCESSION NP_116563<br>VERSION NP_116563.1 | Val30-Ala214 |
| TNFRSF7 | CD27, MGC20393, S152, T14, Tp55 | ACCESSION NP_001233<br>VERSION NP_001233.1 | Thr21 – Ser127<br>Thr21 – Ser133<br>Thr21 – Asp188 |
| TNFRSF8 | CD30, D1S166E, KI-1 | ACCESSION NP_001234<br>VERSION NP_001234.2 | Phe19 – Thr173<br>Asp224 – Gly385<br>Phe19 – Gly385 |
| TNFRSF9 | 4-1BB, CD137, CDw137, ILA, MGC2172 | ACCESSION NP_001552<br>VERSION NP_001552.2 | Leu24 – Ser145<br>Leu24 – Ser171<br>Leu24 – Gly182 |
| TNFRSF10a | APO2, CD261, DR4, MGC9365, TRAILR-1, TRAILR1 | ACCESSION NP_003835<br>VERSION NP_003835.2 | Ala24 – Ser234<br>Ala24 - Gly235<br>Gly129 – Ser234<br>Glu130 – Ser234<br>Gly129 – Gly235<br>Glu130 – Gly235 |
| TNFRSF10b | CD262, DR5, KILLER, KILLER/DR5, TRAIL-R2, TRAILR2, TRICK2, TRICK2A, TRICK2B, TRICKB, ZTNFR9 | ACCESSION NP_003833<br>VERSION NP_003833.3 | Glu53 – Gly184<br>Ala55 – Gly184<br>Ser77 – Gly184<br>Glu78 – Gly184<br>Glu78 – Ser201 |
| TNFRSF10c | CD263, DCR1, LIT, TRAILR3, TRID | ACCESSION NP_003832<br>VERSION NP_003832.2 | Tyr24 – Ala155<br>Ser25 – Ala155<br>Gly50 – Ala155<br>Tyr24 – Ser238<br>Ser25 – Ser238<br>Gly50 – Ser238 |
| TNFRSF10d | CD264, DCR2, TRAILR4, TRUNDD | ACCESSION NP_003831<br>VERSION NP_003831.2 | Ala56 – Ser184<br>Ala56 – Ser187<br>Ala56 – Gly190<br>Leu78 – Ser184<br>Leu78– Ser187<br>Leu78 – Gly190<br>Glu80 – Ser184<br>Glu80– Ser187 |

Figure 6B

| receptor | aliases | reference-sequence a | LBD definition b |
|---|---|---|---|
| | | | Glu80 – Gly190 |
| TNFRSF11a | CD265, ODFR, OFE, RANK, TRANCER | ACCESSION NP_003830<br>VERSION NP_003830.1 | Ala22,Arg23 – Ser197<br>Ala22,Arg23 – Glu206<br>Ala22,Arg23 – His208<br>Ala22,Arg23 - Ala200<br>Leu28 – Ser197<br>Leu28 – Glu206<br>Leu28 – His208<br>Leu28 – Ala200 |
| TNFRSF11b | MGC29565, OCIF, OPG, TR1 | ACCESSION NP_002537<br>VERSION NP_002537.3 | Thr19; Gln20,Glu21 – Ala205<br>Thr19; Gln20,Glu21 – Leu401 |
| TNFRSF12a | Fn14 | ACCESSION BAA94792<br>VERSION BAA94792.1 | Glu28 – Ala70<br>Glu28 – Ala73 |
| TNFRSF13b | CD267, CVID, FLJ39942, MGC133214, MGC39952, TACI, TNFRSF14B | ACCESSION NP_036584<br>VERSION NP_036584.1 | Ser2 – Q159<br>Ser2 – Ser110<br>Ser2 – Pro111<br>Asp16 - Q159<br>Asp16 – Ser110<br>Asp16– Pro111<br>Glu19 – Q159<br>Glu19 – Ser110<br>Glu19 – Pro111<br>Ser68 – Ser110<br>Ser68 – Q159 |
| TNFRSF13c | CTA-250D10.7, BAFF-R, BAFFR, CD268, MGC138235 | ACCESSION NP_443177<br>VERSION NP_443177.1 | Asp13 – Ala71<br>Asp13 – Glu69 |
| TNFRSF14 | ATAR, HVEA, HVEM, LIGHTR, TR2 | ACCESSION NP_003811<br>VERSION NP_003811.2 | Pro37,Leu39 – Ser145, Gly154, Gly193, Gly195,Ser199 |
| TNFRSF16 | NGFR, CD271, p75(NTR) | ACCESSION NP_002498<br>VERSION NP_002498.1 | Gly27, Lys28, Glu29 – Glu190,<br>Gly193,Thr200,<br>Gly204, Gly246 |
| TNFRSF17 | BCM, BCMA, CD269 | ACCESSION NP_001183<br>VERSION NP_001183.2 | Ala5 - Gly51 |
| TNFRSF18-var1 | AITR, GITR, GITR-D | ACCESSION NP_004186<br>VERSION NP_004186.1 | Gln26 – Gly138, Gly145, Gly156, Gly164 |
| TNFRSF18-var2 | AITR, GITR, GITR-D | ACCESSION NP_683699<br>VERSION NP_683699.1 | Gln26 – Ser255 |
| TNFRSF19 | TAJ, TAJ-alpha, TRADE, TROY | ACCESSION NP_061117<br>VERSION NP_061117.2 | Lys26 – Gly139<br>Lys26 – Ser176<br>Gly21 – Ser144 |
| TNFRSF19L<br>L = Like | FLJ14993, RELT | ACCESSION NP_116260<br>VERSION NP_116260.2 | Ser2, Thr25 – Gly125, Gly154, Thr159 |

Figure 6C

| receptor | aliases | reference-sequence[a] | LBD definition[b] |
|---|---|---|---|
| TNFRSF21 | BM-018, DR6, MGC31965 | ACCESSION NP_055267<br>VERSION NP_055267.1 | Gln42; Gln63 –<br>Ser218, Gly226 |
| TNFRSF25-var1 | APO-3, DDR3, DR3, LARD, TNFRSF12, TR3, TRAMP, WSL-1, WSL-LR | ACCESSION NP_683866<br>VERSION NP_683866.1 | Gln25 – Thr181,<br>Gly208 |
| TNFRSF25-var2 | APO-3, DDR3, DR3, LARD, TNFRSF12, TR3, TRAMP, WSL-1, WSL-LR | ACCESSION NP_003781<br>VERSION NP_003781.1 | Gln25 – Gly196;<br>Gln199 |
| TNFRSF25-var3 | APO-3, DDR3, DR3, LARD, TNFRSF12, TR3, TRAMP, WSL-1, WSL-LR | ACCESSION NP_683867<br>VERSION NP_683867.1 | Gln25 – Thr181,<br>Gly203 |
| TNFRSF25-var4 | APO-3, DDR3, DR3, LARD, TNFRSF12, TR3, TRAMP, WSL-1, WSL-LR | ACCESSION NP_683868<br>VERSION NP_683868.1 | Gln25 – Gln151 |
| TNFRSF27 | EDA2R, EDA-A2R, EDAA2R, XEDAR | ACCESSION NP_068555<br>VERSION NP_068555.1 | Asp2 – Ser123,<br>Asp128, Thr131 | a Reference sequences refer to NCBI database entries
b LBD = ligand-binding domain, defining preferred regions for trimeric TNFR-S proteins

SEQUENCE LISTING

<160> NUMBER OF SEQ ID NOS: 61

<210> SEQ ID NO 1
<211> LENGTH: 455

```
<212> TYPE: PRT
<213> ORGANISM: Homo sapiens

<400> SEQUENCE: 1

Met Gly Leu Ser Thr Val Pro Asp Leu Leu Leu Pro Leu Val Leu Leu
1               5                   10                  15

Glu Leu Leu Val Gly Ile Tyr Pro Ser Gly Val Ile Gly Leu Val Pro
            20                  25                  30

His Leu Gly Asp Arg Glu Lys Arg Asp Ser Val Cys Pro Gln Gly Lys
        35                  40                  45

Tyr Ile His Pro Gln Asn Asn Ser Ile Cys Cys Thr Lys Cys His Lys
    50                  55                  60

Gly Thr Tyr Leu Tyr Asn Asp Cys Pro Gly Pro Gly Gln Asp Thr Asp
65                  70                  75                  80

Cys Arg Glu Cys Glu Ser Gly Ser Phe Thr Ala Ser Glu Asn His Leu
                85                  90                  95

Arg His Cys Leu Ser Cys Ser Lys Cys Arg Lys Glu Met Gly Gln Val
            100                 105                 110

Glu Ile Ser Ser Cys Thr Val Asp Arg Asp Thr Val Cys Gly Cys Arg
        115                 120                 125

Lys Asn Gln Tyr Arg His Tyr Trp Ser Glu Asn Leu Phe Gln Cys Phe
130                 135                 140

Asn Cys Ser Leu Cys Leu Asn Gly Thr Val His Leu Ser Cys Gln Glu
145                 150                 155                 160

Lys Gln Asn Thr Val Cys Thr Cys His Ala Gly Phe Phe Leu Arg Glu
                165                 170                 175

Asn Glu Cys Val Ser Cys Ser Asn Cys Lys Lys Ser Leu Glu Cys Thr
            180                 185                 190

Lys Leu Cys Leu Pro Gln Ile Glu Asn Val Lys Gly Thr Glu Asp Ser
        195                 200                 205

Gly Thr Thr Val Leu Leu Pro Leu Val Ile Phe Phe Gly Leu Cys Leu
210                 215                 220

Leu Ser Leu Leu Phe Ile Gly Leu Met Tyr Arg Tyr Gln Arg Trp Lys
225                 230                 235                 240

Ser Lys Leu Tyr Ser Ile Val Cys Gly Lys Ser Thr Pro Glu Lys Glu
                245                 250                 255

Gly Glu Leu Glu Gly Thr Thr Thr Lys Pro Leu Ala Pro Asn Pro Ser
            260                 265                 270

Phe Ser Pro Thr Pro Gly Phe Thr Pro Thr Leu Gly Phe Ser Pro Val
        275                 280                 285

Pro Ser Ser Thr Phe Thr Ser Ser Ser Thr Tyr Thr Pro Gly Asp Cys
290                 295                 300

Pro Asn Phe Ala Ala Pro Arg Arg Glu Val Ala Pro Pro Tyr Gln Gly
305                 310                 315                 320

Ala Asp Pro Ile Leu Ala Thr Ala Leu Ala Ser Asp Pro Ile Pro Asn
                325                 330                 335

Pro Leu Gln Lys Trp Glu Asp Ser Ala His Lys Pro Gln Ser Leu Asp
            340                 345                 350

Thr Asp Asp Pro Ala Thr Leu Tyr Ala Val Val Glu Asn Val Pro Pro
        355                 360                 365

Leu Arg Trp Lys Glu Phe Val Arg Arg Leu Gly Leu Ser Asp His Glu
370                 375                 380

Ile Asp Arg Leu Glu Leu Gln Asn Gly Arg Cys Leu Arg Glu Ala Gln
385                 390                 395                 400
```

-continued

```
Tyr Ser Met Leu Ala Thr Trp Arg Arg Thr Pro Arg Arg Glu Ala
                    405                 410                 415

Thr Leu Glu Leu Leu Gly Arg Val Leu Arg Asp Met Asp Leu Gly
            420                 425                 430

Cys Leu Glu Asp Ile Glu Glu Ala Leu Cys Gly Pro Ala Ala Leu Pro
            435                 440                 445

Pro Ala Pro Ser Leu Leu Arg
450                 455

<210> SEQ ID NO 2
<211> LENGTH: 461
<212> TYPE: PRT
<213> ORGANISM: Homo sapiens

<400> SEQUENCE: 2

Met Ala Pro Val Ala Val Trp Ala Ala Leu Ala Val Gly Leu Glu Leu
1               5                   10                  15

Trp Ala Ala Ala His Ala Leu Pro Ala Gln Val Ala Phe Thr Pro Tyr
            20                  25                  30

Ala Pro Glu Pro Gly Ser Thr Cys Arg Leu Arg Glu Tyr Tyr Asp Gln
        35                  40                  45

Thr Ala Gln Met Cys Cys Ser Lys Cys Ser Pro Gly Gln His Ala Lys
50                  55                  60

Val Phe Cys Thr Lys Thr Ser Asp Thr Val Cys Asp Ser Cys Glu Asp
65                  70                  75                  80

Ser Thr Tyr Thr Gln Leu Trp Asn Trp Val Pro Glu Cys Leu Ser Cys
                85                  90                  95

Gly Ser Arg Cys Ser Ser Asp Gln Val Glu Thr Gln Ala Cys Thr Arg
            100                 105                 110

Glu Gln Asn Arg Ile Cys Thr Cys Arg Pro Gly Trp Tyr Cys Ala Leu
        115                 120                 125

Ser Lys Gln Glu Gly Cys Arg Leu Cys Ala Pro Leu Arg Lys Cys Arg
130                 135                 140

Pro Gly Phe Gly Val Ala Arg Pro Gly Thr Glu Thr Ser Asp Val Val
145                 150                 155                 160

Cys Lys Pro Cys Ala Pro Gly Thr Phe Ser Asn Thr Thr Ser Ser Thr
                165                 170                 175

Asp Ile Cys Arg Pro His Gln Ile Cys Asn Val Val Ala Ile Pro Gly
            180                 185                 190

Asn Ala Ser Met Asp Ala Val Cys Thr Ser Thr Ser Pro Thr Arg Ser
        195                 200                 205

Met Ala Pro Gly Ala Val His Leu Pro Gln Pro Val Ser Thr Arg Ser
210                 215                 220

Gln His Thr Gln Pro Thr Pro Glu Pro Ser Thr Ala Pro Ser Thr Ser
225                 230                 235                 240

Phe Leu Leu Pro Met Gly Pro Ser Pro Pro Ala Glu Gly Ser Thr Gly
                245                 250                 255

Asp Phe Ala Leu Pro Val Gly Leu Ile Val Gly Val Thr Ala Leu Gly
            260                 265                 270

Leu Leu Ile Ile Gly Val Val Asn Cys Val Ile Met Thr Gln Val Lys
        275                 280                 285

Lys Lys Pro Leu Cys Leu Gln Arg Glu Ala Lys Val Pro His Leu Pro
290                 295                 300

Ala Asp Lys Ala Arg Gly Thr Gln Gly Pro Glu Gln Gln His Leu Leu
305                 310                 315                 320
```

```
Ile Thr Ala Pro Ser Ser Ser Ser Ser Leu Glu Ser Ala Ser
            325                 330                 335

Ala Leu Asp Arg Arg Ala Pro Thr Arg Asn Gln Pro Gln Ala Pro Gly
            340                 345                 350

Val Glu Ala Ser Gly Ala Gly Glu Ala Arg Ala Ser Thr Gly Ser Ser
            355                 360                 365

Asp Ser Ser Pro Gly Gly His Gly Thr Gln Val Asn Val Thr Cys Ile
            370                 375                 380

Val Asn Val Cys Ser Ser Ser Asp His Ser Ser Gln Cys Ser Ser Gln
385                 390                 395                 400

Ala Ser Ser Thr Met Gly Asp Thr Asp Ser Ser Pro Ser Glu Ser Pro
            405                 410                 415

Lys Asp Glu Gln Val Pro Phe Ser Lys Glu Glu Cys Ala Phe Arg Ser
            420                 425                 430

Gln Leu Glu Thr Pro Glu Thr Leu Leu Gly Ser Thr Glu Glu Lys Pro
            435                 440                 445

Leu Pro Leu Gly Val Pro Asp Ala Gly Met Lys Pro Ser
            450                 455                 460

<210> SEQ ID NO 3
<211> LENGTH: 435
<212> TYPE: PRT
<213> ORGANISM: Homo sapiens

<400> SEQUENCE: 3

Met Leu Leu Pro Trp Ala Thr Ser Ala Pro Gly Leu Ala Trp Gly Pro
1               5                   10                  15

Leu Val Leu Gly Leu Phe Gly Leu Leu Ala Ala Ser Gln Pro Gln Ala
            20                  25                  30

Val Pro Pro Tyr Ala Ser Glu Asn Gln Thr Cys Arg Asp Gln Glu Lys
            35                  40                  45

Glu Tyr Tyr Glu Pro Gln His Arg Ile Cys Cys Ser Arg Cys Pro Pro
        50                  55                  60

Gly Thr Tyr Val Ser Ala Lys Cys Ser Arg Ile Arg Asp Thr Val Cys
65                  70                  75                  80

Ala Thr Cys Ala Glu Asn Ser Tyr Asn Glu His Trp Asn Tyr Leu Thr
                85                  90                  95

Ile Cys Gln Leu Cys Arg Pro Cys Asp Pro Val Met Gly Leu Glu Glu
            100                 105                 110

Ile Ala Pro Cys Thr Ser Lys Arg Lys Thr Gln Cys Arg Cys Gln Pro
            115                 120                 125

Gly Met Phe Cys Ala Ala Trp Ala Leu Glu Cys Thr His Cys Glu Leu
130                 135                 140

Leu Ser Asp Cys Pro Pro Gly Thr Glu Ala Glu Leu Lys Asp Glu Val
145                 150                 155                 160

Gly Lys Gly Asn Asn His Cys Val Pro Cys Lys Ala Gly His Phe Gln
            165                 170                 175

Asn Thr Ser Ser Pro Ser Ala Arg Cys Gln Pro His Thr Arg Cys Glu
            180                 185                 190

Asn Gln Gly Leu Val Glu Ala Ala Pro Gly Thr Ala Gln Ser Asp Thr
            195                 200                 205

Thr Cys Lys Asn Pro Leu Glu Pro Leu Pro Pro Glu Met Ser Gly Thr
        210                 215                 220

Met Leu Met Leu Ala Val Leu Leu Pro Leu Ala Phe Phe Leu Leu Leu
225                 230                 235                 240
```

-continued

```
Ala Thr Val Phe Ser Cys Ile Trp Lys Ser His Pro Ser Leu Cys Arg
                245                 250                 255

Lys Leu Gly Ser Leu Leu Lys Arg Arg Pro Gln Gly Glu Gly Pro Asn
            260                 265                 270

Pro Val Ala Gly Ser Trp Glu Pro Pro Lys Ala His Pro Tyr Phe Pro
        275                 280                 285

Asp Leu Val Gln Pro Leu Leu Pro Ile Ser Gly Asp Val Ser Pro Val
    290                 295                 300

Ser Thr Gly Leu Pro Ala Ala Pro Val Leu Glu Ala Gly Val Pro Gln
305                 310                 315                 320

Gln Gln Ser Pro Leu Asp Leu Thr Arg Glu Pro Gln Leu Glu Pro Gly
                325                 330                 335

Glu Gln Ser Gln Val Ala His Gly Thr Asn Gly Ile His Val Thr Gly
            340                 345                 350

Gly Ser Met Thr Ile Thr Gly Asn Ile Tyr Ile Tyr Asn Gly Pro Val
        355                 360                 365

Leu Gly Gly Pro Pro Gly Pro Gly Asp Leu Pro Ala Thr Pro Glu Pro
    370                 375                 380

Pro Tyr Pro Ile Pro Glu Glu Gly Asp Pro Gly Pro Gly Leu Ser
385                 390                 395                 400

Thr Pro His Gln Glu Asp Gly Lys Ala Trp His Leu Ala Glu Thr Glu
                405                 410                 415

His Cys Gly Ala Thr Pro Ser Asn Arg Gly Pro Arg Asn Gln Phe Ile
            420                 425                 430

Thr His Asp
        435

<210> SEQ ID NO 4
<211> LENGTH: 277
<212> TYPE: PRT
<213> ORGANISM: Homo sapiens

<400> SEQUENCE: 4

Met Cys Val Gly Ala Arg Arg Leu Gly Arg Gly Pro Cys Ala Ala Leu
1               5                   10                  15

Leu Leu Leu Gly Leu Gly Leu Ser Thr Val Thr Gly Leu His Cys Val
            20                  25                  30

Gly Asp Thr Tyr Pro Ser Asn Asp Arg Cys Cys His Glu Cys Arg Pro
        35                  40                  45

Gly Asn Gly Met Val Ser Arg Cys Ser Arg Ser Gln Asn Thr Val Cys
    50                  55                  60

Arg Pro Cys Gly Pro Gly Phe Tyr Asn Asp Val Val Ser Ser Lys Pro
65                  70                  75                  80

Cys Lys Pro Cys Thr Trp Cys Asn Leu Arg Ser Gly Ser Glu Arg Lys
                85                  90                  95

Gln Leu Cys Thr Ala Thr Gln Asp Thr Val Cys Arg Cys Arg Ala Gly
            100                 105                 110

Thr Gln Pro Leu Asp Ser Tyr Lys Pro Gly Val Asp Cys Ala Pro Cys
        115                 120                 125

Pro Pro Gly His Phe Ser Pro Gly Asp Asn Gln Ala Cys Lys Pro Trp
    130                 135                 140

Thr Asn Cys Thr Leu Ala Gly Lys His Thr Leu Gln Pro Ala Ser Asn
145                 150                 155                 160

Ser Ser Asp Ala Ile Cys Glu Asp Arg Asp Pro Pro Ala Thr Gln Pro
                165                 170                 175
```

-continued

```
Gln Glu Thr Gln Gly Pro Pro Ala Arg Pro Ile Thr Val Gln Pro Thr
            180                 185                 190

Glu Ala Trp Pro Arg Thr Ser Gln Gly Pro Ser Thr Arg Pro Val Glu
        195                 200                 205

Val Pro Gly Gly Arg Ala Val Ala Ala Ile Leu Gly Leu Gly Leu Val
    210                 215                 220

Leu Gly Leu Leu Gly Pro Leu Ala Ile Leu Leu Ala Leu Tyr Leu Leu
225                 230                 235                 240

Arg Arg Asp Gln Arg Leu Pro Pro Asp Ala His Lys Pro Pro Gly Gly
                245                 250                 255

Gly Ser Phe Arg Thr Pro Ile Gln Glu Glu Gln Ala Asp Ala His Ser
            260                 265                 270

Thr Leu Ala Lys Ile
            275

<210> SEQ ID NO 5
<211> LENGTH: 277
<212> TYPE: PRT
<213> ORGANISM: Homo sapiens

<400> SEQUENCE: 5

Met Val Arg Leu Pro Leu Gln Cys Val Leu Trp Gly Cys Leu Leu Thr
1               5                   10                  15

Ala Val His Pro Glu Pro Pro Thr Ala Cys Arg Glu Lys Gln Tyr Leu
            20                  25                  30

Ile Asn Ser Gln Cys Cys Ser Leu Cys Gln Pro Gly Gln Lys Leu Val
        35                  40                  45

Ser Asp Cys Thr Glu Phe Thr Glu Thr Glu Cys Leu Pro Cys Gly Glu
    50                  55                  60

Ser Glu Phe Leu Asp Thr Trp Asn Arg Glu Thr His Cys His Gln His
65                  70                  75                  80

Lys Tyr Cys Asp Pro Asn Leu Gly Leu Arg Val Gln Gln Lys Gly Thr
                85                  90                  95

Ser Glu Thr Asp Thr Ile Cys Thr Cys Glu Glu Gly Trp His Cys Thr
            100                 105                 110

Ser Glu Ala Cys Glu Ser Cys Val Leu His Arg Ser Cys Ser Pro Gly
        115                 120                 125

Phe Gly Val Lys Gln Ile Ala Thr Gly Val Ser Asp Thr Ile Cys Glu
    130                 135                 140

Pro Cys Pro Val Gly Phe Phe Ser Asn Val Ser Ser Ala Phe Glu Lys
145                 150                 155                 160

Cys His Pro Trp Thr Ser Cys Glu Thr Lys Asp Leu Val Val Gln Gln
                165                 170                 175

Ala Gly Thr Asn Lys Thr Asp Val Val Cys Gly Pro Gln Asp Arg Leu
            180                 185                 190

Arg Ala Leu Val Val Ile Pro Ile Ile Phe Gly Ile Leu Phe Ala Ile
        195                 200                 205

Leu Leu Val Leu Val Phe Ile Lys Lys Val Ala Lys Lys Pro Thr Asn
    210                 215                 220

Lys Ala Pro His Pro Lys Gln Glu Pro Gln Glu Ile Asn Phe Pro Asp
225                 230                 235                 240

Asp Leu Pro Gly Ser Asn Thr Ala Ala Pro Val Gln Glu Thr Leu His
                245                 250                 255

Gly Cys Gln Pro Val Thr Gln Glu Asp Gly Lys Glu Ser Arg Ile Ser
            260                 265                 270
```

Val Gln Glu Arg Gln
         275

<210> SEQ ID NO 6
<211> LENGTH: 335
<212> TYPE: PRT
<213> ORGANISM: Homo sapiens

<400> SEQUENCE: 6

Met Leu Gly Ile Trp Thr Leu Leu Pro Leu Val Leu Thr Ser Val Ala
1               5                   10                  15

Arg Leu Ser Ser Lys Ser Val Asn Ala Gln Val Thr Asp Ile Asn Ser
            20                  25                  30

Lys Gly Leu Glu Leu Arg Lys Thr Val Thr Thr Val Glu Thr Gln Asn
        35                  40                  45

Leu Glu Gly Leu His His Asp Gly Gln Phe Cys His Lys Pro Cys Pro
    50                  55                  60

Pro Gly Glu Arg Lys Ala Arg Asp Cys Thr Val Asn Gly Asp Glu Pro
65                  70                  75                  80

Asp Cys Val Pro Cys Gln Glu Gly Lys Glu Tyr Thr Asp Lys Ala His
                85                  90                  95

Phe Ser Ser Lys Cys Arg Arg Cys Arg Leu Cys Asp Glu Gly His Gly
            100                 105                 110

Leu Glu Val Glu Ile Asn Cys Thr Arg Thr Gln Asn Thr Lys Cys Arg
        115                 120                 125

Cys Lys Pro Asn Phe Phe Cys Asn Ser Thr Val Cys Glu His Cys Asp
    130                 135                 140

Pro Cys Thr Lys Cys Glu His Gly Ile Ile Lys Glu Cys Thr Leu Thr
145                 150                 155                 160

Ser Asn Thr Lys Cys Lys Glu Glu Gly Ser Arg Ser Asn Leu Gly Trp
                165                 170                 175

Leu Cys Leu Leu Leu Leu Pro Ile Pro Leu Ile Val Trp Val Lys Arg
            180                 185                 190

Lys Glu Val Gln Lys Thr Cys Arg Lys His Arg Lys Glu Asn Gln Gly
        195                 200                 205

Ser His Glu Ser Pro Thr Leu Asn Pro Glu Thr Val Ala Ile Asn Leu
    210                 215                 220

Ser Asp Val Asp Leu Ser Lys Tyr Ile Thr Thr Ile Ala Gly Val Met
225                 230                 235                 240

Thr Leu Ser Gln Val Lys Gly Phe Val Arg Lys Asn Gly Val Asn Glu
                245                 250                 255

Ala Lys Ile Asp Glu Ile Lys Asn Asp Asn Val Gln Asp Thr Ala Glu
            260                 265                 270

Gln Lys Val Gln Leu Leu Arg Asn Trp His Gln Leu His Gly Lys Lys
        275                 280                 285

Glu Ala Tyr Asp Thr Leu Ile Lys Asp Leu Lys Lys Ala Asn Leu Cys
    290                 295                 300

Thr Leu Ala Glu Lys Ile Gln Thr Ile Ile Leu Lys Asp Ile Thr Ser
305                 310                 315                 320

Asp Ser Glu Asn Ser Asn Phe Arg Asn Glu Ile Gln Ser Leu Val
                325                 330                 335

<210> SEQ ID NO 7
<211> LENGTH: 300
<212> TYPE: PRT
<213> ORGANISM: Homo sapiens -continued

<400> SEQUENCE: 7

```
Met Arg Ala Leu Glu Gly Pro Gly Leu Ser Leu Leu Cys Leu Val Leu
1               5                   10                  15

Ala Leu Pro Ala Leu Leu Pro Val Pro Ala Val Arg Gly Val Ala Glu
            20                  25                  30

Thr Pro Thr Tyr Pro Trp Arg Asp Ala Glu Thr Gly Glu Arg Leu Val
        35                  40                  45

Cys Ala Gln Cys Pro Pro Gly Thr Phe Val Gln Arg Pro Cys Arg Arg
    50                  55                  60

Asp Ser Pro Thr Thr Cys Gly Pro Cys Pro Arg His Tyr Thr Gln
65                  70                  75                  80

Phe Trp Asn Tyr Leu Glu Arg Cys Arg Tyr Cys Asn Val Leu Cys Gly
                85                  90                  95

Glu Arg Glu Glu Ala Arg Ala Cys His Ala Thr His Asn Arg Ala
            100                 105                 110

Cys Arg Cys Arg Thr Gly Phe Phe Ala His Ala Gly Phe Cys Leu Glu
            115                 120                 125

His Ala Ser Cys Pro Pro Gly Ala Gly Val Ile Ala Pro Gly Thr Pro
            130                 135                 140

Ser Gln Asn Thr Gln Cys Gln Pro Cys Pro Pro Gly Thr Phe Ser Ala
145                 150                 155                 160

Ser Ser Ser Ser Glu Gln Cys Gln Pro His Arg Asn Cys Thr Ala
                165                 170                 175

Leu Gly Leu Ala Leu Asn Val Pro Gly Ser Ser Ser His Asp Thr Leu
            180                 185                 190

Cys Thr Ser Cys Thr Gly Phe Pro Leu Ser Thr Arg Val Pro Gly Ala
            195                 200                 205

Glu Glu Cys Glu Arg Ala Val Ile Asp Phe Val Ala Phe Gln Asp Ile
            210                 215                 220

Ser Ile Lys Arg Leu Gln Arg Leu Leu Gln Ala Leu Glu Ala Pro Glu
225                 230                 235                 240

Gly Trp Gly Pro Thr Pro Arg Ala Gly Arg Ala Ala Leu Gln Leu Lys
                245                 250                 255

Leu Arg Arg Arg Leu Thr Glu Leu Leu Gly Ala Gln Asp Gly Ala Leu
            260                 265                 270

Leu Val Arg Leu Leu Gln Ala Leu Arg Val Ala Arg Met Pro Gly Leu
            275                 280                 285

Glu Arg Ser Val Arg Glu Arg Phe Leu Pro Val His
            290                 295                 300

<210> SEQ ID NO 8
<211> LENGTH: 260
<212> TYPE: PRT
<213> ORGANISM: Homo sapiens

<400> SEQUENCE: 8

Met Ala Arg Pro His Pro Trp Trp Leu Cys Val Leu Gly Thr Leu Val
1               5                   10                  15

Gly Leu Ser Ala Thr Pro Ala Pro Lys Ser Cys Pro Glu Arg His Tyr
            20                  25                  30

Trp Ala Gln Gly Lys Leu Cys Cys Gln Met Cys Glu Pro Gly Thr Phe
            35                  40                  45

Leu Val Lys Asp Cys Asp Gln His Arg Lys Ala Ala Gln Cys Asp Pro
        50                  55                  60

Cys Ile Pro Gly Val Ser Phe Ser Pro Asp His His Thr Arg Pro His
```

-continued

```
                65                  70                  75                  80
Cys Glu Ser Cys Arg His Cys Asn Ser Gly Leu Leu Val Arg Asn Cys
                    85                  90                  95

Thr Ile Thr Ala Asn Ala Glu Cys Ala Cys Arg Asn Gly Trp Gln Cys
                100                 105                 110

Arg Asp Lys Glu Cys Thr Glu Cys Asp Pro Leu Pro Asn Pro Ser Leu
            115                 120                 125

Thr Ala Arg Ser Ser Gln Ala Leu Ser Pro His Pro Gln Pro Thr His
        130                 135                 140

Leu Pro Tyr Val Ser Glu Met Leu Glu Ala Arg Thr Ala Gly His Met
145                 150                 155                 160

Gln Thr Leu Ala Asp Phe Arg Gln Leu Pro Ala Arg Thr Leu Ser Thr
                165                 170                 175

His Trp Pro Pro Gln Arg Ser Leu Cys Ser Ser Asp Phe Ile Arg Ile
                180                 185                 190

Leu Val Ile Phe Ser Gly Met Phe Leu Val Phe Thr Leu Ala Gly Ala
            195                 200                 205

Leu Phe Leu His Gln Arg Arg Lys Tyr Arg Ser Asn Lys Gly Glu Ser
        210                 215                 220

Pro Val Glu Pro Ala Glu Pro Cys Arg Tyr Ser Cys Pro Arg Glu Glu
225                 230                 235                 240

Glu Gly Ser Thr Ile Pro Ile Gln Glu Asp Tyr Arg Lys Pro Glu Pro
                245                 250                 255

Ala Cys Ser Pro
                260

<210> SEQ ID NO 9
<211> LENGTH: 595
<212> TYPE: PRT
<213> ORGANISM: Homo sapiens

<400> SEQUENCE: 9

Met Arg Val Leu Leu Ala Ala Leu Gly Leu Leu Phe Leu Gly Ala Leu
1               5                   10                  15

Arg Ala Phe Pro Gln Asp Arg Pro Phe Glu Asp Thr Cys His Gly Asn
                20                  25                  30

Pro Ser His Tyr Tyr Asp Lys Ala Val Arg Arg Cys Cys Tyr Arg Cys
            35                  40                  45

Pro Met Gly Leu Phe Pro Thr Gln Gln Cys Pro Gln Arg Pro Thr Asp
        50                  55                  60

Cys Arg Lys Gln Cys Glu Pro Asp Tyr Tyr Leu Asp Glu Ala Asp Arg
65                  70                  75                  80

Cys Thr Ala Cys Val Thr Cys Ser Arg Asp Asp Leu Val Glu Lys Thr
                85                  90                  95

Pro Cys Ala Trp Asn Ser Ser Arg Val Cys Glu Cys Arg Pro Gly Met
            100                 105                 110

Phe Cys Ser Thr Ser Ala Val Asn Ser Cys Ala Arg Cys Phe Phe His
        115                 120                 125

Ser Val Cys Pro Ala Gly Met Ile Val Lys Phe Pro Gly Thr Ala Gln
    130                 135                 140

Lys Asn Thr Val Cys Glu Pro Ala Ser Pro Gly Val Ser Pro Ala Cys
145                 150                 155                 160

Ala Ser Pro Glu Asn Cys Lys Glu Pro Ser Ser Gly Thr Ile Pro Gln
                165                 170                 175

Ala Lys Pro Thr Pro Val Ser Pro Ala Thr Ser Ser Ala Ser Thr Met
```

```
            180             185             190
Pro Val Arg Gly Gly Thr Arg Leu Ala Gln Glu Ala Ala Ser Lys Leu
            195             200             205

Thr Arg Ala Pro Asp Ser Pro Ser Ser Val Gly Arg Pro Ser Ser Asp
210             215             220

Pro Gly Leu Ser Pro Thr Gln Pro Cys Pro Glu Gly Ser Gly Asp Cys
225             230             235             240

Arg Lys Gln Cys Glu Pro Asp Tyr Tyr Leu Asp Glu Ala Gly Arg Cys
            245             250             255

Thr Ala Cys Val Ser Cys Ser Arg Asp Asp Leu Val Glu Lys Thr Pro
            260             265             270

Cys Ala Trp Asn Ser Ser Arg Thr Cys Glu Cys Arg Pro Gly Met Ile
            275             280             285

Cys Ala Thr Ser Ala Thr Asn Ser Arg Ala Arg Cys Val Pro Tyr Pro
            290             295             300

Ile Cys Ala Ala Glu Thr Val Thr Lys Pro Gln Asp Met Ala Glu Lys
305             310             315             320

Asp Thr Thr Phe Glu Ala Pro Leu Gly Thr Gln Pro Asp Cys Asn
            325             330             335

Pro Thr Pro Glu Asn Gly Glu Ala Pro Ala Ser Thr Ser Pro Thr Gln
            340             345             350

Ser Leu Leu Val Asp Ser Gln Ala Ser Lys Thr Leu Pro Ile Pro Thr
            355             360             365

Ser Ala Pro Val Ala Leu Ser Ser Thr Gly Lys Pro Val Leu Asp Ala
370             375             380

Gly Pro Val Leu Phe Trp Val Ile Leu Val Leu Val Val Val Val Gly
385             390             395             400

Ser Ser Ala Phe Leu Leu Cys His Arg Arg Ala Cys Arg Lys Arg Ile
            405             410             415

Arg Gln Lys Leu His Leu Cys Tyr Pro Val Gln Thr Ser Gln Pro Lys
            420             425             430

Leu Glu Leu Val Asp Ser Arg Pro Arg Arg Ser Ser Thr Gln Leu Arg
            435             440             445

Ser Gly Ala Ser Val Thr Glu Pro Val Ala Glu Glu Arg Gly Leu Met
450             455             460

Ser Gln Pro Leu Met Glu Thr Cys His Ser Val Gly Ala Ala Tyr Leu
465             470             475             480

Glu Ser Leu Pro Leu Gln Asp Ala Ser Pro Ala Gly Gly Pro Ser Ser
            485             490             495

Pro Arg Asp Leu Pro Glu Pro Arg Val Ser Thr Glu His Thr Asn Asn
            500             505             510

Lys Ile Glu Lys Ile Tyr Ile Met Lys Ala Asp Thr Val Ile Val Gly
            515             520             525

Thr Val Lys Ala Glu Leu Pro Glu Gly Arg Gly Leu Ala Gly Pro Ala
            530             535             540

Glu Pro Glu Leu Glu Glu Glu Leu Glu Ala Asp His Thr Pro His Tyr
545             550             555             560

Pro Glu Gln Glu Thr Glu Pro Pro Leu Gly Ser Cys Ser Asp Val Met
            565             570             575

Leu Ser Val Glu Glu Glu Gly Lys Glu Asp Pro Leu Pro Thr Ala Ala
            580             585             590

Ser Gly Lys
            595
```

<210> SEQ ID NO 10
<211> LENGTH: 255
<212> TYPE: PRT
<213> ORGANISM: Homo sapiens

<400> SEQUENCE: 10

Met Gly Asn Ser Cys Tyr Asn Ile Val Ala Thr Leu Leu Leu Val Leu
1               5                   10                  15

Asn Phe Glu Arg Thr Arg Ser Leu Gln Asp Pro Cys Ser Asn Cys Pro
            20                  25                  30

Ala Gly Thr Phe Cys Asp Asn Asn Arg Asn Gln Ile Cys Ser Pro Cys
        35                  40                  45

Pro Pro Asn Ser Phe Ser Ser Ala Gly Gly Gln Arg Thr Cys Asp Ile
50                  55                  60

Cys Arg Gln Cys Lys Gly Val Phe Arg Thr Arg Lys Glu Cys Ser Ser
65                  70                  75                  80

Thr Ser Asn Ala Glu Cys Asp Cys Thr Pro Gly Phe His Cys Leu Gly
                85                  90                  95

Ala Gly Cys Ser Met Cys Glu Gln Asp Cys Lys Gln Gly Gln Glu Leu
            100                 105                 110

Thr Lys Lys Gly Cys Lys Asp Cys Cys Phe Gly Thr Phe Asn Asp Gln
        115                 120                 125

Lys Arg Gly Ile Cys Arg Pro Trp Thr Asn Cys Ser Leu Asp Gly Lys
130                 135                 140

Ser Val Leu Val Asn Gly Thr Lys Glu Arg Asp Val Val Cys Gly Pro
145                 150                 155                 160

Ser Pro Ala Asp Leu Ser Pro Gly Ala Ser Ser Val Thr Pro Pro Ala
                165                 170                 175

Pro Ala Arg Glu Pro Gly His Ser Pro Gln Ile Ile Ser Phe Phe Leu
            180                 185                 190

Ala Leu Thr Ser Thr Ala Leu Leu Phe Leu Leu Phe Phe Leu Thr Leu
        195                 200                 205

Arg Phe Ser Val Val Lys Arg Gly Arg Lys Lys Leu Leu Tyr Ile Phe
210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Glu Gly Gly Cys Glu Leu
                245                 250                 255

<210> SEQ ID NO 11
<211> LENGTH: 468
<212> TYPE: PRT
<213> ORGANISM: Homo sapiens

<400> SEQUENCE: 11

Met Ala Pro Pro Pro Ala Arg Val His Leu Gly Ala Phe Leu Ala Val
1               5                   10                  15

Thr Pro Asn Pro Gly Ser Ala Ala Ser Gly Thr Glu Ala Ala Ala Ala
            20                  25                  30

Thr Pro Ser Lys Val Trp Gly Ser Ser Ala Gly Arg Ile Glu Pro Arg
        35                  40                  45

Gly Gly Gly Arg Gly Ala Leu Pro Thr Ser Met Gly Gln His Gly Pro
50                  55                  60

Ser Ala Arg Ala Arg Ala Gly Arg Ala Pro Gly Pro Arg Pro Ala Arg
65                  70                  75                  80

Glu Ala Ser Pro Arg Leu Arg Val His Lys Thr Phe Lys Phe Val Val

```
                        85                  90                  95
Val Gly Val Leu Leu Gln Val Val Pro Ser Ala Ala Thr Ile Lys
            100                 105                 110
Leu His Asp Gln Ser Ile Gly Thr Gln Gln Trp Glu His Ser Pro Leu
            115                 120                 125
Gly Glu Leu Cys Pro Pro Gly Ser His Arg Ser Glu His Pro Gly Ala
            130                 135                 140
Cys Asn Arg Cys Thr Glu Gly Val Gly Tyr Thr Asn Ala Ser Asn Asn
145                 150                 155                 160
Leu Phe Ala Cys Leu Pro Cys Thr Ala Cys Lys Ser Asp Glu Glu Glu
                165                 170                 175
Arg Ser Pro Cys Thr Thr Thr Arg Asn Thr Ala Cys Gln Cys Lys Pro
                180                 185                 190
Gly Thr Phe Arg Asn Asp Asn Ser Ala Glu Met Cys Arg Lys Cys Ser
                195                 200                 205
Arg Gly Cys Pro Arg Gly Met Val Lys Val Lys Asp Cys Thr Pro Trp
            210                 215                 220
Ser Asp Ile Glu Cys Val His Lys Glu Ser Gly Asn Gly His Asn Ile
225                 230                 235                 240
Trp Val Ile Leu Val Val Thr Leu Val Val Pro Leu Leu Leu Val Ala
                245                 250                 255
Val Leu Ile Val Cys Cys Cys Ile Gly Ser Gly Cys Gly Gly Asp Pro
                260                 265                 270
Lys Cys Met Asp Arg Val Cys Phe Trp Arg Leu Gly Leu Leu Arg Gly
                275                 280                 285
Pro Gly Ala Glu Asp Asn Ala His Asn Glu Ile Leu Ser Asn Ala Asp
            290                 295                 300
Ser Leu Ser Thr Phe Val Ser Glu Gln Gln Met Glu Ser Gln Glu Pro
305                 310                 315                 320
Ala Asp Leu Thr Gly Val Thr Val Gln Ser Pro Gly Glu Ala Gln Cys
                325                 330                 335
Leu Leu Gly Pro Ala Glu Ala Glu Gly Ser Gln Arg Arg Arg Leu Leu
                340                 345                 350
Val Pro Ala Asn Gly Ala Asp Pro Thr Glu Thr Leu Met Leu Phe Phe
                355                 360                 365
Asp Lys Phe Ala Asn Ile Val Pro Phe Asp Ser Trp Asp Gln Leu Met
                370                 375                 380
Arg Gln Leu Asp Leu Thr Lys Asn Glu Ile Asp Val Val Arg Ala Gly
385                 390                 395                 400
Thr Ala Gly Pro Gly Asp Ala Leu Tyr Ala Met Leu Met Lys Trp Val
                405                 410                 415
Asn Lys Thr Gly Arg Asn Ala Ser Ile His Thr Leu Leu Asp Ala Leu
                420                 425                 430
Glu Arg Met Glu Glu Arg His Ala Lys Glu Lys Ile Gln Asp Leu Leu
                435                 440                 445
Val Asp Ser Gly Lys Phe Ile Tyr Leu Glu Asp Gly Thr Gly Ser Ala
            450                 455                 460
Val Ser Leu Glu
465

<210> SEQ ID NO 12
<211> LENGTH: 440
<212> TYPE: PRT
<213> ORGANISM: Homo sapiens
```

<400> SEQUENCE: 12

```
Met Glu Gln Arg Gly Gln Asn Ala Pro Ala Ser Gly Ala Arg Lys
1               5                   10                  15

Arg His Gly Pro Gly Pro Arg Glu Ala Arg Gly Ala Arg Pro Gly Leu
                20                  25                  30

Arg Val Pro Lys Thr Leu Val Leu Val Val Ala Ala Val Leu Leu Leu
            35                  40                  45

Val Ser Ala Glu Ser Ala Leu Ile Thr Gln Gln Asp Leu Ala Pro Gln
    50                  55                  60

Gln Arg Ala Ala Pro Gln Gln Lys Arg Ser Ser Pro Ser Glu Gly Leu
65                  70                  75                  80

Cys Pro Pro Gly His His Ile Ser Glu Asp Gly Arg Asp Cys Ile Ser
                85                  90                  95

Cys Lys Tyr Gly Gln Asp Tyr Ser Thr His Trp Asn Asp Leu Leu Phe
            100                 105                 110

Cys Leu Arg Cys Thr Arg Cys Asp Ser Gly Glu Val Glu Leu Ser Pro
        115                 120                 125

Cys Thr Thr Thr Arg Asn Thr Val Cys Gln Cys Glu Glu Gly Thr Phe
130                 135                 140

Arg Glu Glu Asp Ser Pro Glu Met Cys Arg Lys Cys Arg Thr Gly Cys
145                 150                 155                 160

Pro Arg Gly Met Val Lys Val Gly Asp Cys Thr Pro Trp Ser Asp Ile
                165                 170                 175

Glu Cys Val His Lys Glu Ser Gly Thr Lys His Ser Gly Glu Ala Pro
            180                 185                 190

Ala Val Glu Glu Thr Val Thr Ser Ser Pro Gly Thr Pro Ala Ser Pro
        195                 200                 205

Cys Ser Leu Ser Gly Ile Ile Ile Gly Val Thr Val Ala Ala Val Val
210                 215                 220

Leu Ile Val Ala Val Phe Val Cys Lys Ser Leu Leu Trp Lys Lys Val
225                 230                 235                 240

Leu Pro Tyr Leu Lys Gly Ile Cys Ser Gly Gly Gly Asp Pro Glu
                245                 250                 255

Arg Val Asp Arg Ser Ser Gln Arg Pro Gly Ala Glu Asp Asn Val Leu
            260                 265                 270

Asn Glu Ile Val Ser Ile Leu Gln Pro Thr Gln Val Pro Glu Gln Glu
        275                 280                 285

Met Glu Val Gln Glu Pro Ala Glu Pro Thr Gly Val Asn Met Leu Ser
    290                 295                 300

Pro Gly Glu Ser Glu His Leu Leu Glu Pro Ala Glu Ala Glu Arg Ser
305                 310                 315                 320

Gln Arg Arg Arg Leu Leu Val Pro Ala Asn Glu Gly Asp Pro Thr Glu
                325                 330                 335

Thr Leu Arg Gln Cys Phe Asp Asp Phe Ala Asp Leu Val Pro Phe Asp
            340                 345                 350

Ser Trp Glu Pro Leu Met Arg Lys Leu Gly Leu Met Asp Asn Glu Ile
        355                 360                 365

Lys Val Ala Lys Ala Glu Ala Ala Gly His Arg Asp Thr Leu Tyr Thr
    370                 375                 380

Met Leu Ile Lys Trp Val Asn Lys Thr Gly Arg Asp Ala Ser Val His
385                 390                 395                 400

Thr Leu Leu Asp Ala Leu Glu Thr Leu Gly Glu Arg Leu Ala Lys Gln
                405                 410                 415
```

```
Lys Ile Glu Asp His Leu Leu Ser Ser Gly Lys Phe Met Tyr Leu Glu
                420                 425                 430

Gly Asn Ala Asp Ser Ala Met Ser
            435                 440

<210> SEQ ID NO 13
<211> LENGTH: 259
<212> TYPE: PRT
<213> ORGANISM: Homo sapiens

<400> SEQUENCE: 13

Met Ala Arg Ile Pro Lys Thr Leu Lys Phe Val Val Ile Val Ala
1               5                   10                  15

Val Leu Leu Pro Val Leu Ala Tyr Ser Ala Thr Thr Ala Arg Gln Glu
                20                  25                  30

Glu Val Pro Gln Gln Thr Val Ala Pro Gln Gln Arg His Ser Phe
            35                  40                  45

Lys Gly Glu Glu Cys Pro Ala Gly Ser His Arg Ser Glu His Thr Gly
        50                  55                  60

Ala Cys Asn Pro Cys Thr Glu Gly Val Asp Tyr Thr Asn Ala Ser Asn
65                  70                  75                  80

Asn Glu Pro Ser Cys Phe Pro Cys Thr Val Cys Lys Ser Asp Gln Lys
                85                  90                  95

His Lys Ser Ser Cys Thr Met Thr Arg Asp Thr Val Cys Gln Cys Lys
            100                 105                 110

Glu Gly Thr Phe Arg Asn Glu Asn Ser Pro Glu Met Cys Arg Lys Cys
        115                 120                 125

Ser Arg Cys Pro Ser Gly Glu Val Gln Val Ser Asn Cys Thr Ser Trp
130                 135                 140

Asp Asp Ile Gln Cys Val Glu Glu Phe Gly Ala Asn Ala Thr Val Glu
145                 150                 155                 160

Thr Pro Ala Ala Glu Glu Thr Met Asn Thr Ser Pro Gly Thr Pro Ala
                165                 170                 175

Pro Ala Ala Glu Glu Thr Met Asn Thr Ser Pro Gly Thr Pro Ala Pro
            180                 185                 190

Ala Ala Glu Glu Thr Met Thr Thr Ser Pro Gly Thr Pro Ala Pro Ala
        195                 200                 205

Ala Glu Glu Thr Met Thr Thr Ser Pro Gly Thr Pro Ala Pro Ala Ala
        210                 215                 220

Glu Glu Thr Met Thr Thr Ser Pro Gly Thr Pro Ala Ser Ser His Tyr
225                 230                 235                 240

Leu Ser Cys Thr Ile Val Gly Ile Ile Val Leu Ile Val Leu Leu Ile
                245                 250                 255

Val Phe Val

<210> SEQ ID NO 14
<211> LENGTH: 411
<212> TYPE: PRT
<213> ORGANISM: Homo sapiens

<400> SEQUENCE: 14

Met Glu Gln Arg Gly Gln Asn Ala Pro Ala Ala Ser Gly Ala Arg Lys
1               5                   10                  15

Arg His Gly Pro Gly Pro Arg Glu Ala Arg Gly Ala Arg Pro Gly Leu
            20                  25                  30

Arg Val Pro Lys Thr Leu Val Leu Val Val Ala Ala Val Leu Leu Leu
        35                  40                  45
```

Val Ser Ala Glu Ser Ala Leu Ile Thr Gln Gln Asp Leu Ala Pro Gln
 50                  55                  60

Gln Arg Ala Ala Pro Gln Lys Arg Ser Ser Pro Ser Glu Gly Leu
65                  70                  75                  80

Cys Pro Pro Gly His His Ile Ser Glu Asp Gly Arg Asp Cys Ile Ser
                 85                  90                  95

Cys Lys Tyr Gly Gln Asp Tyr Ser Thr His Trp Asn Asp Leu Leu Phe
                100                 105                 110

Cys Leu Arg Cys Thr Arg Cys Asp Ser Gly Glu Val Glu Leu Ser Pro
            115                 120                 125

Cys Thr Thr Thr Arg Asn Thr Val Cys Gln Cys Glu Glu Gly Thr Phe
130                 135                 140

Arg Glu Glu Asp Ser Pro Glu Met Cys Arg Lys Cys Arg Thr Gly Cys
145                 150                 155                 160

Pro Arg Gly Met Val Lys Val Gly Asp Cys Thr Pro Trp Ser Asp Ile
                165                 170                 175

Glu Cys Val His Lys Glu Ser Gly Ile Ile Gly Val Thr Val Ala
                180                 185                 190

Ala Val Val Leu Ile Val Ala Val Phe Val Cys Lys Ser Leu Leu Trp
            195                 200                 205

Lys Lys Val Leu Pro Tyr Leu Lys Gly Ile Cys Ser Gly Gly Gly Gly
210                 215                 220

Asp Pro Glu Arg Val Asp Arg Ser Ser Gln Arg Pro Gly Ala Glu Asp
225                 230                 235                 240

Asn Val Leu Asn Glu Ile Val Ser Ile Leu Gln Pro Thr Gln Val Pro
                245                 250                 255

Glu Gln Glu Met Glu Val Gln Glu Pro Ala Glu Pro Thr Gly Val Asn
                260                 265                 270

Met Leu Ser Pro Gly Glu Ser Glu His Leu Leu Glu Pro Ala Glu Ala
            275                 280                 285

Glu Arg Ser Gln Arg Arg Arg Leu Leu Val Pro Ala Asn Glu Gly Asp
290                 295                 300

Pro Thr Glu Thr Leu Arg Gln Cys Phe Asp Asp Phe Ala Asp Leu Val
305                 310                 315                 320

Pro Phe Asp Ser Trp Glu Pro Leu Met Arg Lys Leu Gly Leu Met Asp
                325                 330                 335

Asn Glu Ile Lys Val Ala Lys Ala Glu Ala Ala Gly His Arg Asp Thr
                340                 345                 350

Leu Tyr Thr Met Leu Ile Lys Trp Val Asn Lys Thr Gly Arg Asp Ala
            355                 360                 365

Ser Val His Thr Leu Leu Asp Ala Leu Glu Thr Leu Gly Glu Arg Leu
            370                 375                 380

Ala Lys Gln Lys Ile Glu Asp His Leu Leu Ser Ser Gly Lys Phe Met
385                 390                 395                 400

Tyr Leu Glu Gly Asn Ala Asp Ser Ala Met Ser
                405                 410

<210> SEQ ID NO 15
<211> LENGTH: 616
<212> TYPE: PRT
<213> ORGANISM: Homo sapiens

<400> SEQUENCE: 15

Met Ala Pro Arg Ala Arg Arg Arg Pro Leu Phe Ala Leu Leu Leu
1               5                   10                  15

```
Leu Cys Ala Leu Leu Ala Arg Leu Gln Val Ala Leu Gln Ile Ala Pro
            20                  25                  30

Pro Cys Thr Ser Glu Lys His Tyr Glu His Leu Gly Arg Cys Cys Asn
        35                  40                  45

Lys Cys Glu Pro Gly Lys Tyr Met Ser Ser Lys Cys Thr Thr Thr Ser
50                  55                  60

Asp Ser Val Cys Leu Pro Cys Gly Pro Asp Glu Tyr Leu Asp Ser Trp
65                  70                  75                  80

Asn Glu Glu Asp Lys Cys Leu Leu His Lys Val Cys Asp Thr Gly Lys
                85                  90                  95

Ala Leu Val Ala Val Ala Gly Asn Ser Thr Thr Pro Arg Arg Cys
                100                 105                 110

Ala Cys Thr Ala Gly Tyr His Trp Ser Gln Asp Cys Glu Cys Arg
        115                 120                 125

Arg Asn Thr Glu Cys Ala Pro Gly Leu Gly Ala Gln His Pro Leu Gln
    130                 135                 140

Leu Asn Lys Asp Thr Val Cys Lys Pro Cys Leu Ala Gly Tyr Phe Ser
145                 150                 155                 160

Asp Ala Phe Ser Ser Thr Asp Lys Cys Arg Pro Trp Thr Asn Cys Thr
                165                 170                 175

Phe Leu Gly Lys Arg Val Glu His His Gly Thr Glu Lys Ser Asp Ala
            180                 185                 190

Val Cys Ser Ser Ser Leu Pro Ala Arg Lys Pro Pro Asn Glu Pro His
        195                 200                 205

Val Tyr Leu Pro Gly Leu Ile Ile Leu Leu Leu Phe Ala Ser Val Ala
210                 215                 220

Leu Val Ala Ala Ile Ile Phe Gly Val Cys Tyr Arg Lys Lys Gly Lys
225                 230                 235                 240

Ala Leu Thr Ala Asn Leu Trp His Trp Ile Asn Glu Ala Cys Gly Arg
                245                 250                 255

Leu Ser Gly Asp Lys Glu Ser Ser Gly Asp Ser Cys Val Ser Thr His
            260                 265                 270

Thr Ala Asn Phe Gly Gln Gln Gly Ala Cys Glu Gly Val Leu Leu Leu
        275                 280                 285

Thr Leu Glu Glu Lys Thr Phe Pro Glu Asp Met Cys Tyr Pro Asp Gln
290                 295                 300

Gly Gly Val Cys Gln Gly Thr Cys Val Gly Gly Pro Tyr Ala Gln
305                 310                 315                 320

Gly Glu Asp Ala Arg Met Leu Ser Leu Val Ser Lys Thr Glu Ile Glu
                325                 330                 335

Glu Asp Ser Phe Arg Gln Met Pro Thr Glu Asp Glu Tyr Met Asp Arg
            340                 345                 350

Pro Ser Gln Pro Thr Asp Gln Leu Leu Phe Leu Thr Glu Pro Gly Ser
        355                 360                 365

Lys Ser Thr Pro Pro Phe Ser Glu Pro Leu Glu Val Gly Glu Asn Asp
370                 375                 380

Ser Leu Ser Gln Cys Phe Thr Gly Thr Gln Ser Thr Val Gly Ser Glu
385                 390                 395                 400

Ser Cys Asn Cys Thr Glu Pro Leu Cys Arg Thr Asp Trp Thr Pro Met
                405                 410                 415

Ser Ser Glu Asn Tyr Leu Gln Lys Glu Val Asp Ser Gly His Cys Pro
            420                 425                 430

His Trp Ala Ala Ser Pro Ser Pro Asn Trp Ala Asp Val Cys Thr Gly
```

-continued

```
                435                 440                 445
Cys Arg Asn Pro Pro Gly Glu Asp Cys Glu Pro Leu Val Gly Ser Pro
    450                 455                 460

Lys Arg Gly Pro Leu Pro Gln Cys Ala Tyr Gly Met Gly Leu Pro Pro
465                 470                 475                 480

Glu Glu Glu Ala Ser Arg Thr Glu Ala Arg Asp Gln Pro Glu Asp Gly
                485                 490                 495

Ala Asp Gly Arg Leu Pro Ser Ser Ala Arg Ala Gly Ala Gly Ser Gly
                500                 505                 510

Ser Ser Pro Gly Gly Gln Ser Pro Ala Ser Gly Asn Val Thr Gly Asn
            515                 520                 525

Ser Asn Ser Thr Phe Ile Ser Ser Gly Gln Val Met Asn Phe Lys Gly
        530                 535                 540

Asp Ile Ile Val Val Tyr Val Ser Gln Thr Ser Gln Glu Gly Ala Ala
545                 550                 555                 560

Ala Ala Ala Glu Pro Met Gly Arg Pro Val Gln Glu Glu Thr Leu Ala
                565                 570                 575

Arg Arg Asp Ser Phe Ala Gly Asn Gly Pro Arg Phe Pro Asp Pro Cys
            580                 585                 590

Gly Gly Pro Glu Gly Leu Arg Glu Pro Glu Lys Ala Ser Arg Pro Val
        595                 600                 605

Gln Glu Gln Gly Gly Ala Lys Ala
    610                 615

<210> SEQ ID NO 16
<211> LENGTH: 401
<212> TYPE: PRT
<213> ORGANISM: Homo sapiens

<400> SEQUENCE: 16

Met Asn Asn Leu Leu Cys Cys Ala Leu Val Phe Leu Asp Ile Ser Ile
1               5                   10                  15

Lys Trp Thr Thr Gln Glu Thr Phe Pro Pro Lys Tyr Leu His Tyr Asp
            20                  25                  30

Glu Glu Thr Ser His Gln Leu Leu Cys Asp Lys Cys Pro Pro Gly Thr
        35                  40                  45

Tyr Leu Lys Gln His Cys Thr Ala Lys Trp Lys Thr Val Cys Ala Pro
    50                  55                  60

Cys Pro Asp His Tyr Tyr Thr Asp Ser Trp His Thr Ser Asp Glu Cys
65                  70                  75                  80

Leu Tyr Cys Ser Pro Val Cys Lys Glu Leu Gln Tyr Val Lys Gln Glu
                85                  90                  95

Cys Asn Arg Thr His Asn Arg Val Cys Glu Cys Lys Glu Gly Arg Tyr
            100                 105                 110

Leu Glu Ile Glu Phe Cys Leu Lys His Arg Ser Cys Pro Pro Gly Phe
        115                 120                 125

Gly Val Val Gln Ala Gly Thr Pro Glu Arg Asn Thr Val Cys Lys Arg
    130                 135                 140

Cys Pro Asp Gly Phe Phe Ser Asn Glu Thr Ser Ser Lys Ala Pro Cys
145                 150                 155                 160

Arg Lys His Thr Asn Cys Ser Val Phe Gly Leu Leu Leu Thr Gln Lys
                165                 170                 175

Gly Asn Ala Thr His Asp Asn Ile Cys Ser Gly Asn Ser Glu Ser Thr
            180                 185                 190

Gln Lys Cys Gly Ile Asp Val Thr Leu Cys Glu Glu Ala Phe Phe Arg
```

```
                195                 200                 205

Phe Ala Val Pro Thr Lys Phe Thr Pro Asn Trp Leu Ser Val Leu Val
210                 215                 220

Asp Asn Leu Pro Gly Thr Lys Val Asn Ala Glu Ser Val Glu Arg Ile
225                 230                 235                 240

Lys Arg Gln His Ser Ser Gln Glu Gln Thr Phe Gln Leu Leu Lys Leu
                245                 250                 255

Trp Lys His Gln Asn Lys Asp Gln Asp Ile Val Lys Ile Ile Gln
                260                 265                 270

Asp Ile Asp Leu Cys Glu Asn Ser Val Gln Arg His Ile Gly His Ala
275                 280                 285

Asn Leu Thr Phe Glu Gln Leu Arg Ser Leu Met Glu Ser Leu Pro Gly
290                 295                 300

Lys Lys Val Gly Ala Glu Asp Ile Glu Lys Thr Ile Lys Ala Cys Lys
305                 310                 315                 320

Pro Ser Asp Gln Ile Leu Lys Leu Leu Ser Leu Trp Arg Ile Lys Asn
                325                 330                 335

Gly Asp Gln Asp Thr Leu Lys Gly Leu Met His Ala Leu Lys His Ser
                340                 345                 350

Lys Thr Tyr His Phe Pro Lys Thr Val Thr Gln Ser Leu Lys Lys Thr
                355                 360                 365

Ile Arg Phe Leu His Ser Phe Thr Met Tyr Lys Leu Tyr Gln Lys Leu
370                 375                 380

Phe Leu Glu Met Ile Gly Asn Gln Val Gln Ser Val Lys Ile Ser Cys
385                 390                 395                 400

Leu

<210> SEQ ID NO 17
<211> LENGTH: 129
<212> TYPE: PRT
<213> ORGANISM: Homo sapiens

<400> SEQUENCE: 17

Met Ala Arg Gly Ser Leu Arg Arg Leu Leu Arg Leu Leu Val Leu Gly
1               5                   10                  15

Leu Trp Leu Ala Leu Leu Arg Ser Val Ala Gly Glu Gln Ala Pro Gly
                20                  25                  30

Thr Ala Pro Cys Ser Arg Gly Ser Ser Trp Ser Ala Asp Leu Asp Lys
                35                  40                  45

Cys Met Asp Cys Ala Ser Cys Arg Ala Arg Pro His Ser Asp Phe Cys
50                  55                  60

Leu Gly Cys Ala Ala Ala Pro Pro Ala Pro Phe Arg Leu Leu Trp Pro
65                  70                  75                  80

Ile Leu Gly Gly Ala Leu Ser Leu Thr Phe Val Leu Gly Leu Leu Ser
                85                  90                  95

Gly Phe Leu Val Trp Arg Arg Cys Arg Arg Arg Glu Lys Phe Thr Thr
                100                 105                 110

Pro Ile Glu Glu Thr Gly Gly Glu Gly Cys Pro Ala Val Ala Leu Ile
                115                 120                 125

Gln

<210> SEQ ID NO 18
<211> LENGTH: 293
<212> TYPE: PRT
<213> ORGANISM: Homo sapiens
```

<400> SEQUENCE: 18

```
Met Ser Gly Leu Gly Arg Ser Arg Gly Gly Arg Ser Arg Val Asp
1               5                   10                  15

Gln Glu Glu Arg Phe Pro Gln Gly Leu Trp Thr Gly Val Ala Met Arg
            20                  25                  30

Ser Cys Pro Glu Glu Gln Tyr Trp Asp Pro Leu Leu Gly Thr Cys Met
        35                  40                  45

Ser Cys Lys Thr Ile Cys Asn His Gln Ser Gln Arg Thr Cys Ala Ala
    50                  55                  60

Phe Cys Arg Ser Leu Ser Cys Arg Lys Glu Gln Gly Lys Phe Tyr Asp
65              70                  75                  80

His Leu Leu Arg Asp Cys Ile Ser Cys Ala Ser Ile Cys Gly Gln His
                85                  90                  95

Pro Lys Gln Cys Ala Tyr Phe Cys Glu Asn Lys Leu Arg Ser Pro Val
            100                 105                 110

Asn Leu Pro Pro Glu Leu Arg Arg Gln Arg Ser Gly Glu Val Glu Asn
        115                 120                 125

Asn Ser Asp Asn Ser Gly Arg Tyr Gln Gly Leu Glu His Arg Gly Ser
    130                 135                 140

Glu Ala Ser Pro Ala Leu Pro Gly Leu Lys Leu Ser Ala Asp Gln Val
145             150                 155                 160

Ala Leu Val Tyr Ser Thr Leu Gly Leu Cys Leu Cys Ala Val Leu Cys
                165                 170                 175

Cys Phe Leu Val Ala Val Ala Cys Phe Leu Lys Lys Arg Gly Asp Pro
            180                 185                 190

Cys Ser Cys Gln Pro Arg Ser Arg Pro Arg Gln Ser Pro Ala Lys Ser
        195                 200                 205

Ser Gln Asp His Ala Met Glu Ala Gly Ser Pro Val Ser Thr Ser Pro
    210                 215                 220

Glu Pro Val Glu Thr Cys Ser Phe Cys Phe Pro Glu Cys Arg Ala Pro
225             230                 235                 240

Thr Gln Glu Ser Ala Val Thr Pro Gly Thr Pro Asp Pro Thr Cys Ala
                245                 250                 255

Gly Arg Trp Gly Cys His Thr Arg Thr Thr Val Leu Gln Pro Cys Pro
            260                 265                 270

His Ile Pro Asp Ser Gly Leu Gly Ile Val Cys Val Pro Ala Gln Glu
        275                 280                 285

Gly Gly Pro Gly Ala
    290
```

<210> SEQ ID NO 19
<211> LENGTH: 184
<212> TYPE: PRT
<213> ORGANISM: Homo sapiens

<400> SEQUENCE: 19

```
Met Arg Arg Gly Pro Arg Ser Leu Arg Gly Arg Asp Ala Pro Ala Pro
1               5                   10                  15

Thr Pro Cys Val Pro Ala Glu Cys Phe Asp Leu Leu Val Arg His Cys
            20                  25                  30

Val Ala Cys Gly Leu Leu Arg Thr Pro Arg Pro Lys Pro Ala Gly Ala
        35                  40                  45

Ser Ser Pro Ala Pro Arg Thr Ala Leu Gln Pro Gln Glu Ser Val Gly
    50                  55                  60

Ala Gly Ala Gly Glu Ala Ala Leu Pro Leu Pro Gly Leu Leu Phe Gly
```

```
                65                  70                  75                  80
Ala Pro Ala Leu Leu Gly Leu Ala Leu Val Leu Ala Leu Val Leu Val
                            85                  90                  95

Gly Leu Val Ser Trp Arg Arg Arg Gln Arg Leu Arg Gly Ala Ser
                100                 105                 110

Ser Ala Glu Ala Pro Asp Gly Asp Lys Asp Ala Pro Glu Pro Leu Asp
                115                 120                 125

Lys Val Ile Ile Leu Ser Pro Gly Ile Ser Asp Ala Thr Ala Pro Ala
            130                 135                 140

Trp Pro Pro Pro Gly Glu Asp Pro Gly Thr Thr Pro Pro Gly His Ser
145                 150                 155                 160

Val Pro Val Pro Ala Thr Glu Leu Gly Ser Thr Glu Leu Val Thr Thr
                165                 170                 175

Lys Thr Ala Gly Pro Glu Gln Gln
                180

<210> SEQ ID NO 20
<211> LENGTH: 283
<212> TYPE: PRT
<213> ORGANISM: Homo sapiens

<400> SEQUENCE: 20

Met Glu Pro Pro Gly Asp Trp Gly Pro Pro Pro Trp Arg Ser Thr Pro
1               5                   10                  15

Lys Thr Asp Val Leu Arg Leu Val Leu Tyr Leu Thr Phe Leu Gly Ala
                20                  25                  30

Pro Cys Tyr Ala Pro Ala Leu Pro Ser Cys Lys Glu Asp Glu Tyr Pro
            35                  40                  45

Val Gly Ser Glu Cys Cys Pro Lys Cys Ser Pro Gly Tyr Arg Val Lys
    50                  55                  60

Glu Ala Cys Gly Glu Leu Thr Gly Thr Val Cys Glu Pro Cys Pro Pro
65                  70                  75                  80

Gly Thr Tyr Ile Ala His Leu Asn Gly Leu Ser Lys Cys Leu Gln Cys
                85                  90                  95

Gln Met Cys Asp Pro Ala Met Gly Leu Arg Ala Ser Arg Asn Cys Ser
                100                 105                 110

Arg Thr Glu Asn Ala Val Cys Gly Cys Ser Pro Gly His Phe Cys Ile
            115                 120                 125

Val Gln Asp Gly Asp His Cys Ala Ala Cys Arg Ala Tyr Ala Thr Ser
    130                 135                 140

Ser Pro Gly Gln Arg Val Gln Lys Gly Gly Thr Glu Ser Gln Asp Thr
145                 150                 155                 160

Leu Cys Gln Asn Cys Pro Pro Gly Thr Phe Ser Pro Asn Gly Thr Leu
                165                 170                 175

Glu Glu Cys Gln His Gln Thr Lys Cys Ser Trp Leu Val Thr Lys Ala
                180                 185                 190

Gly Ala Gly Thr Ser Ser Ser His Trp Val Trp Trp Phe Leu Ser Gly
            195                 200                 205

Ser Leu Val Ile Val Ile Val Cys Ser Thr Val Gly Leu Ile Ile Cys
    210                 215                 220

Val Lys Arg Arg Lys Pro Arg Gly Asp Val Val Lys Val Ile Val Ser
225                 230                 235                 240

Val Gln Arg Lys Arg Gln Glu Ala Glu Gly Glu Ala Thr Val Ile Glu
                245                 250                 255

Ala Leu Gln Ala Pro Pro Asp Val Thr Thr Val Ala Val Glu Glu Thr
```

```
                   260             265                 270
Ile Pro Ser Phe Thr Gly Arg Ser Pro Asn His
            275                 280
```

<210> SEQ ID NO 21
<211> LENGTH: 427
<212> TYPE: PRT
<213> ORGANISM: Homo sapiens

<400> SEQUENCE: 21

```
Met Gly Ala Gly Ala Thr Gly Arg Ala Met Asp Gly Pro Arg Leu Leu
1               5                   10                  15

Leu Leu Leu Leu Leu Gly Val Ser Leu Gly Gly Ala Lys Glu Ala Cys
            20                  25                  30

Pro Thr Gly Leu Tyr Thr His Ser Gly Glu Cys Cys Lys Ala Cys Asn
        35                  40                  45

Leu Gly Glu Gly Val Ala Gln Pro Cys Gly Ala Asn Gln Thr Val Cys
    50                  55                  60

Glu Pro Cys Leu Asp Ser Val Thr Phe Ser Asp Val Val Ser Ala Thr
65                  70                  75                  80

Glu Pro Cys Lys Pro Cys Thr Glu Cys Val Gly Leu Gln Ser Met Ser
                85                  90                  95

Ala Pro Cys Val Glu Ala Asp Asp Ala Val Cys Arg Cys Ala Tyr Gly
            100                 105                 110

Tyr Tyr Gln Asp Glu Thr Thr Gly Arg Cys Glu Ala Cys Arg Val Cys
        115                 120                 125

Glu Ala Gly Ser Gly Leu Val Phe Ser Cys Gln Asp Lys Gln Asn Thr
    130                 135                 140

Val Cys Glu Glu Cys Pro Asp Gly Thr Tyr Ser Asp Glu Ala Asn His
145                 150                 155                 160

Val Asp Pro Cys Leu Pro Cys Thr Val Cys Glu Asp Thr Glu Arg Gln
                165                 170                 175

Leu Arg Glu Cys Thr Arg Trp Ala Asp Ala Glu Cys Glu Glu Ile Pro
            180                 185                 190

Gly Arg Trp Ile Thr Arg Ser Thr Pro Pro Glu Gly Ser Asp Ser Thr
        195                 200                 205

Ala Pro Ser Thr Gln Glu Pro Glu Ala Pro Pro Glu Gln Asp Leu Ile
    210                 215                 220

Ala Ser Thr Val Ala Gly Val Val Thr Thr Val Met Gly Ser Ser Gln
225                 230                 235                 240

Pro Val Val Thr Arg Gly Thr Thr Asp Asn Leu Ile Pro Val Tyr Cys
                245                 250                 255

Ser Ile Leu Ala Ala Val Val Val Gly Leu Val Ala Tyr Ile Ala Phe
            260                 265                 270

Lys Arg Trp Asn Ser Cys Lys Gln Asn Lys Gln Gly Ala Asn Ser Arg
        275                 280                 285

Pro Val Asn Gln Thr Pro Pro Pro Glu Gly Glu Lys Leu His Ser Asp
    290                 295                 300

Ser Gly Ile Ser Val Asp Ser Gln Ser Leu His Asp Gln Gln Pro His
305                 310                 315                 320

Thr Gln Thr Ala Ser Gly Gln Ala Leu Lys Gly Asp Gly Gly Leu Tyr
                325                 330                 335

Ser Ser Leu Pro Pro Ala Lys Arg Glu Glu Val Glu Lys Leu Leu Asn
            340                 345                 350

Gly Ser Ala Gly Asp Thr Trp Arg His Leu Ala Gly Glu Leu Gly Tyr
```

```
            355                 360                 365
Gln Pro Glu His Ile Asp Ser Phe Thr His Glu Ala Cys Pro Val Arg
370                 375                 380

Ala Leu Leu Ala Ser Trp Ala Thr Gln Asp Ser Ala Thr Leu Asp Ala
385                 390                 395                 400

Leu Leu Ala Ala Leu Arg Arg Ile Gln Arg Ala Asp Leu Val Glu Ser
                405                 410                 415

Leu Cys Ser Glu Ser Thr Ala Thr Ser Pro Val
            420                 425

<210> SEQ ID NO 22
<211> LENGTH: 184
<212> TYPE: PRT
<213> ORGANISM: Homo sapiens

<400> SEQUENCE: 22

Met Leu Gln Met Ala Gly Gln Cys Ser Gln Asn Glu Tyr Phe Asp Ser
1               5                   10                  15

Leu Leu His Ala Cys Ile Pro Cys Gln Leu Arg Cys Ser Ser Asn Thr
                20                  25                  30

Pro Pro Leu Thr Cys Gln Arg Tyr Cys Asn Ala Ser Val Thr Asn Ser
            35                  40                  45

Val Lys Gly Thr Asn Ala Ile Leu Trp Thr Cys Leu Gly Leu Ser Leu
50                  55                  60

Ile Ile Ser Leu Ala Val Phe Val Leu Met Phe Leu Leu Arg Lys Ile
65                  70                  75                  80

Asn Ser Glu Pro Leu Lys Asp Glu Phe Lys Asn Thr Gly Ser Gly Leu
                85                  90                  95

Leu Gly Met Ala Asn Ile Asp Leu Glu Lys Ser Arg Thr Gly Asp Glu
            100                 105                 110

Ile Ile Leu Pro Arg Gly Leu Glu Tyr Thr Val Glu Glu Cys Thr Cys
        115                 120                 125

Glu Asp Cys Ile Lys Ser Lys Pro Lys Val Asp Ser Asp His Cys Phe
130                 135                 140

Pro Leu Pro Ala Met Glu Glu Gly Ala Thr Ile Leu Val Thr Thr Lys
145                 150                 155                 160

Thr Asn Asp Tyr Cys Lys Ser Leu Pro Ala Ala Leu Ser Ala Thr Glu
                165                 170                 175

Ile Glu Lys Ser Ile Ser Ala Arg
            180

<210> SEQ ID NO 23
<211> LENGTH: 241
<212> TYPE: PRT
<213> ORGANISM: Homo sapiens

<400> SEQUENCE: 23

Met Ala Gln His Gly Ala Met Gly Ala Phe Arg Ala Leu Cys Gly Leu
1               5                   10                  15

Ala Leu Leu Cys Ala Leu Ser Leu Gly Gln Arg Pro Thr Gly Gly Pro
                20                  25                  30

Gly Cys Gly Pro Gly Arg Leu Leu Leu Gly Thr Gly Thr Asp Ala Arg
            35                  40                  45

Cys Cys Arg Val His Thr Thr Arg Cys Cys Arg Asp Tyr Pro Gly Glu
50                  55                  60

Glu Cys Cys Ser Glu Trp Asp Cys Met Cys Val Gln Pro Glu Phe His
65                  70                  75                  80
```

```
Cys Gly Asp Pro Cys Cys Thr Thr Cys Arg His His Pro Cys Pro Pro
                85                  90                  95
Gly Gln Gly Val Gln Ser Gln Gly Lys Phe Ser Phe Gly Phe Gln Cys
                100                 105                 110
Ile Asp Cys Ala Ser Gly Thr Phe Ser Gly Gly His Glu Gly His Cys
                115                 120                 125
Lys Pro Trp Thr Asp Cys Thr Gln Phe Gly Phe Leu Thr Val Phe Pro
                130                 135                 140
Gly Asn Lys Thr His Asn Ala Val Cys Val Pro Gly Ser Pro Pro Ala
145                 150                 155                 160
Glu Pro Leu Gly Trp Leu Thr Val Val Leu Leu Ala Val Ala Ala Cys
                165                 170                 175
Val Leu Leu Leu Thr Ser Ala Gln Leu Gly Leu His Ile Trp Gln Leu
                180                 185                 190
Arg Ser Gln Cys Met Trp Pro Arg Glu Thr Gln Leu Leu Leu Glu Val
                195                 200                 205
Pro Pro Ser Thr Glu Asp Ala Arg Ser Cys Gln Phe Pro Glu Glu Glu
                210                 215                 220
Arg Gly Glu Arg Ser Ala Glu Glu Lys Gly Arg Leu Gly Asp Leu Trp
225                 230                 235                 240
Val

<210> SEQ ID NO 24
<211> LENGTH: 255
<212> TYPE: PRT
<213> ORGANISM: Homo sapiens

<400> SEQUENCE: 24

Met Ala Gln His Gly Ala Met Gly Ala Phe Arg Ala Leu Cys Gly Leu
1               5                   10                  15
Ala Leu Leu Cys Ala Leu Ser Leu Gly Gln Arg Pro Thr Gly Gly Pro
                20                  25                  30
Gly Cys Gly Pro Gly Arg Leu Leu Leu Gly Thr Gly Thr Asp Ala Arg
                35                  40                  45
Cys Cys Arg Val His Thr Thr Arg Cys Cys Arg Asp Tyr Pro Gly Glu
                50                  55                  60
Glu Cys Cys Ser Glu Trp Asp Cys Met Cys Val Gln Pro Glu Phe His
65                  70                  75                  80
Cys Gly Asp Pro Cys Cys Thr Thr Cys Arg His His Pro Cys Pro Pro
                85                  90                  95
Gly Gln Gly Val Gln Ser Gln Gly Lys Phe Ser Phe Gly Phe Gln Cys
                100                 105                 110
Ile Asp Cys Ala Ser Gly Thr Phe Ser Gly Gly His Glu Gly His Cys
                115                 120                 125
Lys Pro Trp Thr Asp Cys Cys Trp Arg Cys Arg Arg Pro Lys Thr
                130                 135                 140
Pro Glu Ala Ala Ser Ser Pro Arg Lys Ser Gly Ala Ser Asp Arg Gln
145                 150                 155                 160
Arg Arg Arg Gly Gly Trp Glu Thr Cys Gly Cys Glu Pro Gly Arg Pro
                165                 170                 175
Pro Gly Pro Pro Thr Ala Ala Ser Pro Ser Pro Gly Ala Pro Gln Ala
                180                 185                 190
Ala Gly Ala Leu Arg Ser Ala Leu Gly Arg Ala Leu Leu Pro Trp Gln
                195                 200                 205
```

```
Gln Lys Trp Val Gln Glu Gly Ser Asp Gln Arg Pro Gly Pro Cys
            210                 215                 220
Ser Ser Ala Ala Ala Gly Pro Cys Arg Arg Glu Arg Glu Thr Gln
225                 230                 235                 240
Ser Trp Pro Pro Ser Ser Leu Ala Gly Pro Asp Gly Val Gly Ser
                245                 250                 255

<210> SEQ ID NO 25
<211> LENGTH: 423
<212> TYPE: PRT
<213> ORGANISM: Homo sapiens

<400> SEQUENCE: 25

Met Ala Leu Lys Val Leu Leu Glu Gln Glu Lys Thr Phe Phe Thr Leu
1               5                   10                  15
Leu Val Leu Leu Gly Tyr Leu Ser Cys Lys Val Thr Cys Glu Ser Gly
                20                  25                  30
Asp Cys Arg Gln Gln Glu Phe Arg Asp Arg Ser Gly Asn Cys Val Pro
            35                  40                  45
Cys Asn Gln Cys Gly Pro Gly Met Glu Leu Ser Lys Glu Cys Gly Phe
        50                  55                  60
Gly Tyr Gly Glu Asp Ala Gln Cys Val Thr Cys Arg Leu His Arg Phe
65                  70                  75                  80
Lys Glu Asp Trp Gly Phe Gln Lys Cys Lys Pro Cys Leu Asp Cys Ala
                85                  90                  95
Val Val Asn Arg Phe Gln Lys Ala Asn Cys Ser Ala Thr Ser Asp Ala
            100                 105                 110
Ile Cys Gly Asp Cys Leu Pro Gly Phe Tyr Arg Lys Thr Lys Leu Val
        115                 120                 125
Gly Phe Gln Asp Met Glu Cys Val Pro Cys Gly Asp Pro Pro Pro Pro
130                 135                 140
Tyr Glu Pro His Cys Ala Ser Lys Val Asn Leu Val Lys Ile Ala Ser
145                 150                 155                 160
Thr Ala Ser Ser Pro Arg Asp Thr Ala Leu Ala Ala Val Ile Cys Ser
                165                 170                 175
Ala Leu Ala Thr Val Leu Leu Ala Leu Leu Ile Leu Cys Val Ile Tyr
            180                 185                 190
Cys Lys Arg Gln Phe Met Glu Lys Lys Pro Ser Trp Ser Leu Arg Ser
        195                 200                 205
Gln Asp Ile Gln Tyr Asn Gly Ser Glu Leu Ser Cys Phe Asp Arg Pro
210                 215                 220
Gln Leu His Glu Tyr Ala His Arg Ala Cys Cys Gln Cys Arg Arg Asp
225                 230                 235                 240
Ser Val Gln Thr Cys Gly Pro Val Arg Leu Leu Pro Ser Met Cys Cys
                245                 250                 255
Glu Glu Ala Cys Ser Pro Asn Pro Ala Thr Leu Gly Cys Gly Val His
            260                 265                 270
Ser Ala Ala Ser Leu Gln Ala Arg Asn Ala Gly Pro Ala Gly Glu Met
        275                 280                 285
Val Pro Thr Phe Phe Gly Ser Leu Thr Gln Ser Ile Cys Gly Glu Phe
290                 295                 300
Ser Asp Ala Trp Pro Leu Met Gln Asn Pro Met Gly Gly Asp Asn Ile
305                 310                 315                 320
Ser Phe Cys Asp Ser Tyr Pro Glu Leu Thr Gly Glu Asp Ile His Ser
                325                 330                 335
```

```
Leu Asn Pro Glu Leu Glu Ser Ser Thr Ser Leu Asp Ser Asn Ser Ser
             340                 345                 350

Gln Asp Leu Val Gly Gly Ala Val Pro Val Gln Ser His Ser Glu Asn
             355                 360                 365

Phe Thr Ala Ala Thr Asp Leu Ser Arg Tyr Asn Asn Thr Leu Val Glu
370                 375                 380

Ser Ala Ser Thr Gln Asp Ala Leu Thr Met Arg Ser Gln Leu Asp Gln
385                 390                 395                 400

Glu Ser Gly Ala Val Ile His Pro Ala Thr Gln Thr Ser Leu Gln Val
                405                 410                 415

Arg Gln Arg Leu Gly Ser Leu
            420

<210> SEQ ID NO 26
<211> LENGTH: 430
<212> TYPE: PRT
<213> ORGANISM: Homo sapiens

<400> SEQUENCE: 26

Met Lys Pro Ser Leu Leu Cys Arg Pro Leu Ser Cys Phe Leu Met Leu
1               5                   10                  15

Leu Pro Trp Pro Leu Ala Thr Leu Thr Ser Thr Thr Leu Trp Gln Cys
             20                  25                  30

Pro Pro Gly Glu Glu Pro Asp Leu Asp Pro Gly Gln Gly Thr Leu Cys
             35                  40                  45

Arg Pro Cys Pro Pro Gly Thr Phe Ser Ala Ala Trp Gly Ser Ser Pro
50                  55                  60

Cys Gln Pro His Ala Arg Cys Ser Leu Trp Arg Arg Leu Glu Ala Gln
65                  70                  75                  80

Val Gly Met Ala Thr Arg Asp Thr Leu Cys Gly Asp Cys Trp Pro Gly
                85                  90                  95

Trp Phe Gly Pro Trp Gly Val Pro Arg Val Pro Cys Gln Pro Cys Ser
            100                 105                 110

Trp Ala Pro Leu Gly Thr His Gly Cys Asp Glu Trp Gly Arg Arg Ala
            115                 120                 125

Arg Arg Gly Val Glu Val Ala Ala Gly Ala Ser Ser Gly Gly Glu Thr
130                 135                 140

Arg Gln Pro Gly Asn Gly Thr Arg Ala Gly Gly Pro Glu Glu Thr Ala
145                 150                 155                 160

Ala Gln Tyr Ala Val Ile Ala Ile Val Pro Val Phe Cys Leu Met Gly
                165                 170                 175

Leu Leu Gly Ile Leu Val Cys Asn Leu Leu Lys Arg Lys Gly Tyr His
            180                 185                 190

Cys Thr Ala His Lys Glu Val Gly Pro Gly Pro Gly Gly Gly Gly Ser
            195                 200                 205

Gly Ile Asn Pro Ala Tyr Arg Thr Glu Asp Ala Asn Glu Asp Thr Ile
            210                 215                 220

Gly Val Leu Val Arg Leu Ile Thr Glu Lys Lys Glu Asn Ala Ala Ala
225                 230                 235                 240

Leu Glu Glu Leu Leu Lys Glu Tyr His Ser Lys Gln Leu Val Gln Thr
                245                 250                 255

Ser His Arg Pro Val Ser Lys Leu Pro Pro Ala Pro Asn Val Pro
            260                 265                 270

His Ile Cys Pro His Arg His Leu His Thr Val Gln Gly Leu Ala
            275                 280                 285
```

```
Ser Leu Ser Gly Pro Cys Cys Ser Arg Cys Ser Gln Lys Lys Trp Pro
        290                 295                 300

Glu Val Leu Leu Ser Pro Glu Ala Val Ala Thr Thr Pro Val Pro
305                 310                 315                 320

Ser Leu Leu Pro Asn Pro Thr Arg Val Pro Lys Ala Gly Ala Lys Ala
                    325                 330                 335

Gly Arg Gln Gly Glu Ile Thr Ile Leu Ser Val Gly Arg Phe Arg Val
                340                 345                 350

Ala Arg Ile Pro Glu Gln Arg Thr Ser Ser Met Val Ser Glu Val Lys
            355                 360                 365

Thr Ile Thr Glu Ala Gly Pro Ser Trp Gly Asp Leu Pro Asp Ser Pro
370                 375                 380

Gln Pro Gly Leu Pro Pro Glu Gln Gln Ala Leu Leu Gly Ser Gly Gly
385                 390                 395                 400

Ser Arg Thr Lys Trp Leu Lys Pro Pro Ala Glu Asn Lys Ala Glu Glu
                    405                 410                 415

Asn Arg Tyr Val Val Arg Leu Ser Glu Ser Asn Leu Val Ile
                420                 425                 430

<210> SEQ ID NO 27
<211> LENGTH: 655
<212> TYPE: PRT
<213> ORGANISM: Homo sapiens

<400> SEQUENCE: 27

Met Gly Thr Ser Pro Ser Ser Thr Ala Leu Ala Ser Cys Ser Arg
1               5                   10                  15

Ile Ala Arg Arg Ala Thr Ala Thr Met Ile Ala Gly Ser Leu Leu Leu
                20                  25                  30

Leu Gly Phe Leu Ser Thr Thr Thr Ala Gln Pro Glu Gln Lys Ala Ser
            35                  40                  45

Asn Leu Ile Gly Thr Tyr Arg His Val Asp Arg Ala Thr Gly Gln Val
        50                  55                  60

Leu Thr Cys Asp Lys Cys Pro Ala Gly Thr Tyr Val Ser Glu His Cys
65              70                  75                  80

Thr Asn Thr Ser Leu Arg Val Cys Ser Ser Cys Pro Val Gly Thr Phe
                85                  90                  95

Thr Arg His Glu Asn Gly Ile Glu Lys Cys His Asp Cys Ser Gln Pro
                100                 105                 110

Cys Pro Trp Pro Met Ile Glu Lys Leu Pro Cys Ala Ala Leu Thr Asp
            115                 120                 125

Arg Glu Cys Thr Cys Pro Pro Gly Met Phe Gln Ser Asn Ala Thr Cys
130                 135                 140

Ala Pro His Thr Val Cys Pro Val Gly Trp Gly Val Arg Lys Lys Gly
145                 150                 155                 160

Thr Glu Thr Glu Asp Val Arg Cys Lys Gln Cys Ala Arg Gly Thr Phe
                165                 170                 175

Ser Asp Val Pro Ser Ser Val Met Lys Cys Lys Ala Tyr Thr Asp Cys
            180                 185                 190

Leu Ser Gln Asn Leu Val Val Ile Lys Pro Gly Thr Lys Glu Thr Asp
        195                 200                 205

Asn Val Cys Gly Thr Leu Pro Ser Phe Ser Ser Ser Thr Ser Pro Ser
    210                 215                 220

Pro Gly Thr Ala Ile Phe Pro Arg Pro Glu His Met Glu Thr His Glu
225                 230                 235                 240
```

```
Val Pro Ser Ser Thr Tyr Val Pro Lys Gly Met Asn Ser Thr Glu Ser
            245                 250                 255

Asn Ser Ser Ala Ser Val Arg Pro Lys Val Leu Ser Ser Ile Gln Glu
        260                 265                 270

Gly Thr Val Pro Asp Asn Thr Ser Ser Ala Arg Gly Lys Glu Asp Val
    275                 280                 285

Asn Lys Thr Leu Pro Asn Leu Gln Val Val Asn His Gln Gln Gly Pro
290                 295                 300

His His Arg His Ile Leu Lys Leu Leu Pro Ser Met Glu Ala Thr Gly
305                 310                 315                 320

Gly Glu Lys Ser Ser Thr Pro Ile Lys Gly Pro Lys Arg Gly His Pro
                325                 330                 335

Arg Gln Asn Leu His Lys His Phe Asp Ile Asn Glu His Leu Pro Trp
            340                 345                 350

Met Ile Val Leu Phe Leu Leu Val Leu Val Val Ile Val Val Cys
        355                 360                 365

Ser Ile Arg Lys Ser Ser Arg Thr Leu Lys Lys Gly Pro Arg Gln Asp
        370                 375                 380

Pro Ser Ala Ile Val Glu Lys Ala Gly Leu Lys Lys Ser Met Thr Pro
385                 390                 395                 400

Thr Gln Asn Arg Glu Lys Trp Ile Tyr Tyr Cys Asn Gly His Gly Ile
                405                 410                 415

Asp Ile Leu Lys Leu Val Ala Ala Gln Val Gly Ser Gln Trp Lys Asp
            420                 425                 430

Ile Tyr Gln Phe Leu Cys Asn Ala Ser Glu Arg Glu Val Ala Ala Phe
        435                 440                 445

Ser Asn Gly Tyr Thr Ala Asp His Glu Arg Ala Tyr Ala Ala Leu Gln
450                 455                 460

His Trp Thr Ile Arg Gly Pro Glu Ala Ser Leu Ala Gln Leu Ile Ser
465                 470                 475                 480

Ala Leu Arg Gln His Arg Arg Asn Asp Val Val Glu Lys Ile Arg Gly
                485                 490                 495

Leu Met Glu Asp Thr Thr Gln Leu Glu Thr Asp Lys Leu Ala Leu Pro
            500                 505                 510

Met Ser Pro Ser Pro Leu Ser Pro Ser Pro Ile Pro Ser Pro Asn Ala
        515                 520                 525

Lys Leu Glu Asn Ser Ala Leu Leu Thr Val Glu Pro Ser Pro Gln Asp
530                 535                 540

Lys Asn Lys Gly Phe Phe Val Asp Glu Ser Glu Pro Leu Leu Arg Cys
545                 550                 555                 560

Asp Ser Thr Ser Ser Gly Ser Ser Ala Leu Ser Arg Asn Gly Ser Phe
                565                 570                 575

Ile Thr Lys Glu Lys Lys Asp Thr Val Leu Arg Gln Val Arg Leu Asp
            580                 585                 590

Pro Cys Asp Leu Gln Pro Ile Phe Asp Asp Met Leu His Phe Leu Asn
        595                 600                 605

Pro Glu Glu Leu Arg Val Ile Glu Glu Ile Pro Gln Ala Glu Asp Lys
        610                 615                 620

Leu Asp Arg Leu Phe Glu Ile Ile Gly Val Lys Ser Gln Glu Ala Ser
625                 630                 635                 640

Gln Thr Leu Leu Asp Ser Val Tyr Ser His Leu Pro Asp Leu Leu
                645                 650                 655
```

<210> SEQ ID NO 28

<211> LENGTH: 426
<212> TYPE: PRT
<213> ORGANISM: Homo sapiens

<400> SEQUENCE: 28

```
Met Glu Gln Arg Pro Arg Gly Cys Ala Ala Val Ala Ala Ala Leu Leu
1               5                   10                  15

Leu Val Leu Leu Gly Ala Arg Ala Gln Gly Gly Thr Arg Ser Pro Arg
            20                  25                  30

Cys Asp Cys Ala Gly Asp Phe His Lys Lys Ile Gly Leu Phe Cys Cys
        35                  40                  45

Arg Gly Cys Pro Ala Gly His Tyr Leu Lys Ala Pro Cys Thr Glu Pro
    50                  55                  60

Cys Gly Asn Ser Thr Cys Leu Val Cys Pro Gln Asp Thr Phe Leu Ala
65                  70                  75                  80

Trp Glu Asn His His Asn Ser Glu Cys Ala Arg Cys Gln Ala Cys Asp
                85                  90                  95

Glu Gln Ala Ser Gln Val Ala Leu Glu Asn Cys Ser Ala Val Ala Asp
            100                 105                 110

Thr Arg Cys Gly Cys Lys Pro Gly Trp Phe Val Glu Cys Gln Val Ser
        115                 120                 125

Gln Cys Val Ser Ser Ser Pro Phe Tyr Cys Gln Pro Cys Leu Asp Cys
    130                 135                 140

Gly Ala Leu His Arg His Thr Arg Leu Leu Cys Ser Arg Arg Asp Thr
145                 150                 155                 160

Asp Cys Gly Thr Cys Leu Pro Gly Phe Tyr Glu His Gly Asp Gly Cys
                165                 170                 175

Val Ser Cys Pro Thr Pro Pro Ser Leu Ala Gly Ala Pro Trp Gly
            180                 185                 190

Ala Val Gln Ser Ala Val Pro Leu Ser Val Ala Gly Gly Arg Val Gly
        195                 200                 205

Val Phe Trp Val Gln Val Leu Leu Ala Gly Leu Val Val Pro Leu Leu
    210                 215                 220

Leu Gly Ala Thr Leu Thr Tyr Thr Tyr Arg His Cys Trp Pro His Lys
225                 230                 235                 240

Pro Leu Val Thr Ala Asp Glu Ala Gly Met Glu Ala Leu Thr Pro Pro
                245                 250                 255

Pro Ala Thr His Leu Ser Pro Leu Asp Ser Ala His Thr Leu Leu Ala
            260                 265                 270

Pro Pro Asp Ser Ser Glu Lys Ile Cys Thr Val Gln Leu Val Gly Asn
        275                 280                 285

Ser Trp Thr Pro Gly Tyr Pro Glu Thr Gln Glu Ala Leu Cys Pro Gln
    290                 295                 300

Val Thr Trp Ser Trp Asp Gln Leu Pro Ser Arg Ala Leu Gly Pro Ala
305                 310                 315                 320

Ala Ala Pro Thr Leu Ser Pro Glu Ser Pro Ala Gly Ser Pro Ala Met
                325                 330                 335

Met Leu Gln Pro Gly Pro Gln Leu Tyr Asp Val Met Asp Ala Val Pro
            340                 345                 350

Ala Arg Arg Trp Lys Glu Phe Val Arg Thr Leu Gly Leu Arg Glu Ala
        355                 360                 365

Glu Ile Glu Ala Val Glu Val Glu Ile Gly Arg Phe Arg Asp Gln Gln
    370                 375                 380

Tyr Glu Met Leu Lys Arg Trp Arg Gln Gln Pro Ala Gly Leu Gly
385                 390                 395                 400
```

```
Ala Val Tyr Ala Ala Leu Glu Arg Met Gly Leu Asp Gly Cys Val Glu
                405                 410                 415
Asp Leu Arg Ser Arg Leu Gln Arg Gly Pro
            420                 425

<210> SEQ ID NO 29
<211> LENGTH: 417
<212> TYPE: PRT
<213> ORGANISM: Homo sapiens

<400> SEQUENCE: 29

Met Glu Gln Arg Pro Arg Gly Cys Ala Ala Val Ala Ala Leu Leu
1               5                   10                  15
Leu Val Leu Leu Gly Ala Arg Ala Gln Gly Gly Thr Arg Ser Pro Arg
            20                  25                  30
Cys Asp Cys Ala Gly Asp Phe His Lys Lys Ile Gly Leu Phe Cys Cys
        35                  40                  45
Arg Gly Cys Pro Ala Gly His Tyr Leu Lys Ala Pro Cys Thr Glu Pro
50                  55                  60
Cys Gly Asn Ser Thr Cys Leu Val Cys Pro Gln Asp Thr Phe Leu Ala
65                  70                  75                  80
Trp Glu Asn His His Asn Ser Glu Cys Ala Arg Cys Gln Ala Cys Asp
                85                  90                  95
Glu Gln Ala Ser Gln Val Ala Leu Glu Asn Cys Ser Ala Val Ala Asp
            100                 105                 110
Thr Arg Cys Gly Cys Lys Pro Gly Trp Phe Val Glu Cys Gln Val Ser
        115                 120                 125
Gln Cys Val Ser Ser Ser Pro Phe Tyr Cys Gln Pro Cys Leu Asp Cys
130                 135                 140
Gly Ala Leu His Arg His Thr Arg Leu Leu Cys Ser Arg Arg Asp Thr
145                 150                 155                 160
Asp Cys Gly Thr Cys Leu Pro Gly Phe Tyr Glu His Gly Asp Gly Cys
                165                 170                 175
Val Ser Cys Pro Thr Ser Thr Leu Gly Ser Cys Pro Glu Arg Cys Ala
            180                 185                 190
Ala Val Cys Gly Trp Arg Gln Met Phe Trp Val Gln Val Leu Leu Ala
        195                 200                 205
Gly Leu Val Val Pro Leu Leu Leu Gly Ala Thr Leu Thr Tyr Thr Tyr
210                 215                 220
Arg His Cys Trp Pro His Lys Pro Leu Val Thr Ala Asp Glu Ala Gly
225                 230                 235                 240
Met Glu Ala Leu Thr Pro Pro Ala Thr His Leu Ser Pro Leu Asp
                245                 250                 255
Ser Ala His Thr Leu Leu Ala Pro Pro Asp Ser Ser Glu Lys Ile Cys
            260                 265                 270
Thr Val Gln Leu Val Gly Asn Ser Trp Thr Pro Gly Tyr Pro Glu Thr
        275                 280                 285
Gln Glu Ala Leu Cys Pro Gln Val Thr Trp Ser Trp Asp Gln Leu Pro
290                 295                 300
Ser Arg Ala Leu Gly Pro Ala Ala Ala Pro Thr Leu Ser Pro Glu Ser
305                 310                 315                 320
Pro Ala Gly Ser Pro Ala Met Met Leu Gln Pro Gly Pro Gln Leu Tyr
                325                 330                 335
Asp Val Met Asp Ala Val Pro Ala Arg Arg Trp Lys Glu Phe Val Arg
            340                 345                 350
```

```
Thr Leu Gly Leu Arg Glu Ala Glu Ile Glu Ala Val Glu Val Glu Ile
            355                 360                 365
Gly Arg Phe Arg Asp Gln Gln Tyr Glu Met Leu Lys Arg Trp Arg Gln
        370                 375                 380
Gln Gln Pro Ala Gly Leu Gly Ala Val Tyr Ala Leu Glu Arg Met
385                 390                 395                 400
Gly Leu Asp Gly Cys Val Glu Asp Leu Arg Ser Arg Leu Gln Arg Gly
                405                 410                 415
Pro

<210> SEQ ID NO 30
<211> LENGTH: 380
<212> TYPE: PRT
<213> ORGANISM: Homo sapiens

<400> SEQUENCE: 30

Met Glu Gln Arg Pro Arg Gly Cys Ala Ala Val Ala Ala Ala Leu Leu
1               5                   10                  15
Leu Val Leu Leu Gly Ala Arg Ala Gln Gly Gly Thr Arg Ser Pro Arg
            20                  25                  30
Cys Asp Cys Ala Gly Asp Phe His Lys Lys Ile Gly Leu Phe Cys Cys
        35                  40                  45
Arg Gly Cys Pro Ala Gly His Tyr Leu Lys Ala Pro Cys Thr Glu Pro
    50                  55                  60
Cys Gly Asn Ser Thr Cys Leu Val Cys Pro Gln Asp Thr Phe Leu Ala
65                  70                  75                  80
Trp Glu Asn His His Asn Ser Glu Cys Ala Arg Cys Gln Ala Cys Asp
                85                  90                  95
Glu Gln Ala Ser Gln Val Ala Leu Glu Asn Cys Ser Ala Val Ala Asp
            100                 105                 110
Thr Arg Cys Gly Cys Lys Pro Gly Trp Phe Val Glu Cys Gln Val Ser
        115                 120                 125
Gln Cys Val Ser Ser Ser Pro Phe Tyr Cys Gln Pro Cys Leu Asp Cys
    130                 135                 140
Gly Ala Leu His Arg His Thr Arg Leu Leu Cys Ser Arg Arg Asp Thr
145                 150                 155                 160
Asp Cys Gly Thr Cys Leu Pro Gly Phe Tyr Glu His Gly Asp Gly Cys
                165                 170                 175
Val Ser Cys Pro Thr Ser Thr Leu Gly Ser Cys Pro Gly Arg Cys Ala
            180                 185                 190
Ala Val Cys Gly Trp Arg Gln Asn Glu Ala Gly Met Glu Ala Leu Thr
        195                 200                 205
Pro Pro Pro Ala Thr His Leu Ser Pro Leu Asp Ser Ala His Thr Leu
    210                 215                 220
Leu Ala Pro Pro Asp Ser Ser Glu Lys Ile Cys Thr Val Gln Leu Val
225                 230                 235                 240
Gly Asn Ser Trp Thr Pro Gly Tyr Pro Glu Thr Gln Glu Ala Leu Cys
                245                 250                 255
Pro Gln Val Thr Trp Ser Trp Asp Gln Leu Pro Ser Arg Ala Leu Gly
            260                 265                 270
Pro Ala Ala Ala Pro Thr Leu Ser Pro Glu Ser Pro Ala Gly Ser Pro
        275                 280                 285
Ala Met Met Leu Gln Pro Gly Pro Gln Leu Tyr Asp Val Met Asp Ala
    290                 295                 300
```

```
Val Pro Ala Arg Arg Trp Lys Glu Phe Val Arg Thr Leu Gly Leu Arg
305                 310                 315                 320

Glu Ala Glu Ile Glu Ala Val Glu Val Glu Ile Gly Arg Phe Arg Asp
            325                 330                 335

Gln Gln Tyr Glu Met Leu Lys Arg Trp Arg Gln Gln Pro Ala Gly
        340                 345                 350

Leu Gly Ala Val Tyr Ala Ala Leu Glu Arg Met Gly Leu Asp Gly Cys
        355                 360                 365

Val Glu Asp Leu Arg Ser Arg Leu Gln Arg Gly Pro
    370                 375                 380

<210> SEQ ID NO 31
<211> LENGTH: 372
<212> TYPE: PRT
<213> ORGANISM: Homo sapiens

<400> SEQUENCE: 31

Met Glu Gln Arg Pro Arg Gly Cys Ala Ala Val Ala Ala Ala Leu Leu
1               5                   10                  15

Leu Val Leu Leu Gly Ala Arg Ala Gln Gly Gly Thr Arg Ser Pro Arg
            20                  25                  30

Cys Asp Cys Ala Gly Asp Phe His Lys Lys Ile Gly Leu Phe Cys Cys
            35                  40                  45

Arg Gly Cys Pro Ala Ala Ser Gln Val Ala Leu Glu Asn Cys Ser Ala
        50                  55                  60

Val Ala Asp Thr Arg Cys Gly Cys Lys Pro Gly Trp Phe Val Glu Cys
65                  70                  75                  80

Gln Val Ser Gln Cys Val Ser Ser Pro Phe Tyr Cys Gln Pro Cys
                85                  90                  95

Leu Asp Cys Gly Ala Leu His Arg His Thr Arg Leu Leu Cys Ser Arg
            100                 105                 110

Arg Asp Thr Asp Cys Gly Thr Cys Leu Pro Gly Phe Tyr Glu His Gly
            115                 120                 125

Asp Gly Cys Val Ser Cys Pro Thr Ser Thr Leu Gly Ser Cys Pro Glu
        130                 135                 140

Arg Cys Ala Ala Val Cys Gly Trp Arg Gln Met Phe Trp Val Gln Val
145                 150                 155                 160

Leu Leu Ala Gly Leu Val Val Pro Leu Leu Leu Gly Ala Thr Leu Thr
                165                 170                 175

Tyr Thr Tyr Arg His Cys Trp Pro His Lys Pro Leu Val Thr Ala Asp
            180                 185                 190

Glu Ala Gly Met Glu Ala Leu Thr Pro Pro Ala Thr His Leu Ser
        195                 200                 205

Pro Leu Asp Ser Ala His Thr Leu Leu Ala Pro Pro Asp Ser Ser Glu
210                 215                 220

Lys Ile Cys Thr Val Gln Leu Val Gly Asn Ser Trp Thr Pro Gly Tyr
225                 230                 235                 240

Pro Glu Thr Gln Glu Ala Leu Cys Pro Gln Val Thr Trp Ser Trp Asp
            245                 250                 255

Gln Leu Pro Ser Arg Ala Leu Gly Pro Ala Ala Ala Pro Thr Leu Ser
        260                 265                 270

Pro Glu Ser Pro Ala Gly Ser Pro Ala Met Met Leu Gln Pro Gly Pro
    275                 280                 285

Gln Leu Tyr Asp Val Met Asp Ala Val Pro Ala Arg Arg Trp Lys Glu
    290                 295                 300
```

```
Phe Val Arg Thr Leu Gly Leu Arg Glu Ala Glu Ile Glu Ala Val Glu
305                 310                 315                 320

Val Glu Ile Gly Arg Phe Arg Asp Gln Gln Tyr Glu Met Leu Lys Arg
            325                 330                 335

Trp Arg Gln Gln Gln Pro Ala Gly Leu Gly Ala Val Tyr Ala Ala Leu
        340                 345                 350

Glu Arg Met Gly Leu Asp Gly Cys Val Glu Asp Leu Arg Ser Arg Leu
    355                 360                 365

Gln Arg Gly Pro
    370

<210> SEQ ID NO 32
<211> LENGTH: 297
<212> TYPE: PRT
<213> ORGANISM: Homo sapiens

<400> SEQUENCE: 32

Met Asp Cys Gln Glu Asn Glu Tyr Trp Asp Gln Trp Gly Arg Cys Val
1               5                   10                  15

Thr Cys Gln Arg Cys Gly Pro Gly Gln Glu Leu Ser Lys Asp Cys Gly
            20                  25                  30

Tyr Gly Glu Gly Gly Asp Ala Tyr Cys Thr Ala Cys Pro Pro Arg Arg
        35                  40                  45

Tyr Lys Ser Ser Trp Gly His His Arg Cys Gln Ser Cys Ile Thr Cys
    50                  55                  60

Ala Val Ile Asn Arg Val Gln Lys Val Asn Cys Thr Ala Thr Ser Asn
65                  70                  75                  80

Ala Val Cys Gly Asp Cys Leu Pro Arg Phe Tyr Arg Lys Thr Arg Ile
                85                  90                  95

Gly Gly Leu Gln Asp Gln Glu Cys Ile Pro Cys Thr Lys Gln Thr Pro
            100                 105                 110

Thr Ser Glu Val Gln Cys Ala Phe Gln Leu Ser Leu Val Glu Ala Asp
        115                 120                 125

Ala Pro Thr Val Pro Pro Gln Glu Ala Thr Leu Val Ala Leu Val Ser
130                 135                 140

Ser Leu Leu Val Val Phe Thr Leu Ala Phe Leu Gly Leu Phe Phe Leu
145                 150                 155                 160

Tyr Cys Lys Gln Phe Phe Asn Arg His Cys Gln Arg Gly Gly Leu Leu
                165                 170                 175

Gln Phe Glu Ala Asp Lys Thr Ala Lys Glu Glu Ser Leu Phe Pro Val
            180                 185                 190

Pro Pro Ser Lys Glu Thr Ser Ala Glu Ser Gln Val Ser Glu Asn Ile
        195                 200                 205

Phe Gln Thr Gln Pro Leu Asn Pro Ile Leu Glu Asp Asp Cys Ser Ser
210                 215                 220

Thr Ser Gly Phe Pro Thr Gln Glu Ser Phe Thr Met Ala Ser Cys Thr
225                 230                 235                 240

Ser Glu Ser His Ser His Trp Val His Ser Pro Ile Glu Cys Thr Glu
                245                 250                 255

Leu Asp Leu Gln Lys Phe Ser Ser Ser Ala Ser Tyr Thr Gly Ala Glu
            260                 265                 270

Thr Leu Gly Gly Asn Thr Val Glu Ser Thr Gly Asp Arg Leu Glu Leu
        275                 280                 285

Asn Val Pro Phe Glu Val Pro Ser Pro
    290                 295
```

-continued

<210> SEQ ID NO 33
<211> LENGTH: 722
<212> TYPE: DNA
<213> ORGANISM: Artificial
<220> FEATURE:
<223> OTHER INFORMATION: SPN-hs95R-AT4-St

<400> SEQUENCE: 33

```
aagctttagg gataacaggg taatagccgc caccatggtg ggcatctgga ccctgctgcc      60
tctggtgctg acctctgtgg ccagactgtc ctccaagtcc gtgaacgccc aggtgaccga     120
catcaactcc aagggcctgg agctgagaaa gaccgtgacc accgtggaga cccagaacct     180
ggagggcctg caccacgatg gccagttctg ccacaagcct tgtcctcccg gcgagagaaa     240
ggccagagac tgtaccgtga acggcgacga gcctgactgt gtgccttgtc aggagggcaa     300
ggagtacacc gacaaggccc acttctcctc caagtgccgg aggtgtaggc tgtgtgatga     360
gggccacggc ctggaggtgg agatcaactg taccccggac cagaacacca agtgccgctg     420
taagcccaac ttcttctgta actccaccgt gtgtgagcac tgtgaccct gtaccaagtg      480
tgagcacggc atcatcaagg agtgtaccct gacctccaat accaagtgta aggaggaggg     540
atcctctggt agcagtggct caagtggttc tggttacata ccggaagctc cgcgtgacgg     600
tcaggcttat gtgcgtaagg acggtgaatg ggtactgctg tctaccttcc tgtctggtcc     660
gagctcaagc tcatctagtg catggtcaca cccgcaattc gagaagtgat aatagcggcc     720
gc                                                                    722
```

<210> SEQ ID NO 34
<211> LENGTH: 224
<212> TYPE: PRT
<213> ORGANISM: Artificial
<220> FEATURE:
<223> OTHER INFORMATION: SPN-hs95R-AT4-St

<400> SEQUENCE: 34

```
Met Val Gly Ile Trp Thr Leu Leu Pro Leu Val Leu Thr Ser Val Ala
1               5                   10                  15

Arg Leu Ser Ser Lys Ser Val Asn Ala Gln Val Thr Asp Ile Asn Ser
            20                  25                  30

Lys Gly Leu Glu Leu Arg Lys Thr Val Thr Thr Val Glu Thr Gln Asn
        35                  40                  45

Leu Glu Gly Leu His His Asp Gly Gln Phe Cys His Lys Pro Cys Pro
    50                  55                  60

Pro Gly Glu Arg Lys Ala Arg Asp Cys Thr Val Asn Gly Asp Glu Pro
65                  70                  75                  80

Asp Cys Val Pro Cys Gln Glu Gly Lys Glu Tyr Thr Asp Lys Ala His
                85                  90                  95

Phe Ser Ser Lys Cys Arg Arg Cys Arg Leu Cys Asp Glu Gly His Gly
            100                 105                 110

Leu Glu Val Glu Ile Asn Cys Thr Arg Thr Gln Asn Thr Lys Cys Arg
        115                 120                 125

Cys Lys Pro Asn Phe Phe Cys Asn Ser Thr Val Cys Glu His Cys Asp
    130                 135                 140

Pro Cys Thr Lys Cys Glu His Gly Ile Ile Lys Glu Cys Thr Leu Thr
145                 150                 155                 160

Ser Asn Thr Lys Cys Lys Glu Glu Gly Ser Ser Gly Ser Gly Ser
                165                 170                 175

Ser Gly Ser Gly Tyr Ile Pro Glu Ala Pro Arg Asp Gly Gln Ala Tyr
```

|     |     |     |     |     | 180 |     |     |     |     | 185 |     |     |     |     | 190 |     |     |
| --- | --- | --- | --- | --- | --- | --- | --- | --- | --- | --- | --- | --- | --- | --- | --- | --- | --- |

Val Arg Lys Asp Gly Glu Trp Val Leu Leu Ser Thr Phe Leu Ser Gly
            195                     200                     205

Pro Ser Ser Ser Ser Ser Ala Trp Ser His Pro Gln Phe Glu Lys
    210                     215                     220

<210> SEQ ID NO 35
<211> LENGTH: 719
<212> TYPE: DNA
<213> ORGANISM: Artificial
<220> FEATURE:
<223> OTHER INFORMATION: SPN-hs95R-A69-St

<400> SEQUENCE: 35

```
aagctttagg gataacaggg taatagccgc caccatggtg ggcatctgga ccctgctgcc      60
tctggtgctg acctctgtgg ccagactgtc ctccaagtcc gtgaacgccc aggtgaccga    120
catcaactcc aagggcctgg agctgagaaa gaccgtgacc accgtggaga cccagaacct    180
ggagggcctg caccacgatg gccagttctg ccacaagcct gtcctcccg gcgagagaaa    240
ggccagagac tgtaccgtga acggcgacga gcctgactgt gtgccttgtc aggagggcaa    300
ggagtacacc gacaaggccc acttctcctc caagtgccgg aggtgtaggc tgtgtgatga    360
gggccacggc ctggaggtgg agatcaactg taccccggacc cagaacacca agtgccgctg    420
taagcccaac ttcttctgta actccaccgt gtgtgagcac tgtgacccct gtaccaagtg    480
tgagcacggc atcatcaagg agtgtaccct gacctccaat accaagtgta aggaggaggg    540
atcctctggt agcagtggct caagtggttc tggatatatc gaagatgctc cttctgacgg    600
caagttctat gtccgaaagg atggtgcttg ggttgaattg cctacagctt caggtccgag    660
ctcaagctca tctagtgcat ggtcacaccc gcaattcgag aagtgataat agcggccgc     719
```

<210> SEQ ID NO 36
<211> LENGTH: 223
<212> TYPE: PRT
<213> ORGANISM: Artificial
<220> FEATURE:
<223> OTHER INFORMATION: SPN-hs95R-A69-St

<400> SEQUENCE: 36

Met Val Gly Ile Trp Thr Leu Leu Pro Leu Val Leu Thr Ser Val Ala
1               5                   10                  15

Arg Leu Ser Ser Lys Ser Val Asn Ala Gln Val Thr Asp Ile Asn Ser
            20                  25                  30

Lys Gly Leu Glu Leu Arg Lys Thr Val Thr Thr Val Glu Thr Gln Asn
        35                  40                  45

Leu Glu Gly Leu His His Asp Gly Gln Phe Cys His Lys Pro Cys Pro
    50                  55                  60

Pro Gly Glu Arg Lys Ala Arg Asp Cys Thr Val Asn Gly Asp Glu Pro
65                  70                  75                  80

Asp Cys Val Pro Cys Gln Glu Gly Lys Glu Tyr Thr Asp Lys Ala His
                85                  90                  95

Phe Ser Ser Lys Cys Arg Arg Cys Arg Leu Cys Asp Glu Gly His Gly
            100                 105                 110

Leu Glu Val Glu Ile Asn Cys Thr Arg Thr Gln Asn Thr Lys Cys Arg
        115                 120                 125

Cys Lys Pro Asn Phe Phe Cys Asn Ser Thr Val Cys Glu His Cys Asp
    130                 135                 140

Pro Cys Thr Lys Cys Glu His Gly Ile Ile Lys Glu Cys Thr Leu Thr 145                 150                 155                 160
Ser Asn Thr Lys Cys Lys Glu Glu Gly Ser Gly Ser Ser Gly Ser
                165                 170                 175

Ser Gly Ser Gly Tyr Ile Glu Asp Ala Pro Ser Asp Gly Lys Phe Tyr
            180                 185                 190

Val Arg Lys Asp Gly Ala Trp Val Glu Leu Pro Thr Ala Ser Gly Pro
        195                 200                 205

Ser Ser Ser Ser Ser Ala Trp Ser His Pro Gln Phe Glu Lys
    210                 215                 220

<210> SEQ ID NO 37
<211> LENGTH: 1109
<212> TYPE: DNA
         <213> ORGANISM: Artificial
<220> FEATURE:
<223> OTHER INFORMATION: SPN-hs95R-ASPD-St

<400> SEQUENCE: 37
aagctttagg gataacaggg taatagccgc caccatggtg gcatctgga ccctgctgcc      60
tctggtgctg acctctgtgg ccagactgtc ctccaagtcc gtgaacgccc aggtgaccga    120
catcaactcc aagggcctgg agctgagaaa gaccgtgacc accgtggaga cccagaacct    180
ggagggcctg caccacgatg ccagttctgc cacaagcct tgtcctcccg gcgagagaaa     240
ggccagagac tgtaccgtga acggcgacga gcctgactgt gtgccttgtc aggagggcaa    300
ggagtacacc gacaaggccc acttctcctc caagtgccgg aggtgtaggc tgtgtgatga    360
gggccacggc ctggaggtgg agatcaactg tacccggacc cagaacacca gtgccgctg     420
taagcccaac ttcttctgta actccaccgt gtgtgagcac tgtgacccct gtaccaagtg    480
tgagcacggc atcatcaagg agtgtaccct gacctccaat accaagtgta aggaggaggg    540
atcctctggt tcgagtggtt cgagtggttc tggattgcca gacgttgctt ctttgagaca    600
acaggttgag gctttgcagg gtcaagtcca gcacttgcag gctgctttct ctcaatacaa    660
gaaggttgag ttgttcccaa acggtcaatc tgttggcgaa aagattttca agactgctgg    720
tttcgtcaaa ccattcacgg aggcacaatt attgtgtact caggctggtg acagttggc    780
ctctccacgt tctgccgctg agaacgccgc cttgcaacag ttggtcgtag ctaagaacga    840
ggctgctttc ttgagcatga ctgattccaa gacagagggc aagttcacct acccaacagg    900
agaatccttg gtctattcta attgggcacc tggagagccc aacgatgatg gcggctcaga    960
ggactgtgtg gaaatcttca ccaatggcaa gtggaatgac agagcttgtg agagaagcg    1020
tttggtggtc tgtgagttcg gaggcagtcc ttcatcttca tctagctctg cctggtcgca   1080
tccacaattc gagaaataat agcggccgc                                     1109

<210> SEQ ID NO 38
<211> LENGTH: 354
<212> TYPE: PRT
<213> ORGANISM: Artificial
<220> FEATURE:
<223> OTHER INFORMATION: SPN-hs95R-ASPD-St

<400> SEQUENCE: 38

Met Val Gly Ile Trp Thr Leu Leu Pro Leu Val Leu Thr Ser Val Ala
1               5                   10                  15

Arg Leu Ser Ser Lys Ser Val Asn Ala Gln Val Thr Asp Ile Asn Ser
            20                  25                  30

Lys Gly Leu Glu Leu Arg Lys Thr Val Thr Thr Val Glu Thr Gln Asn
        35                  40                  45

Leu Glu Gly Leu His His Asp Gly Gln Phe Cys His Lys Pro Cys Pro
 50                  55                  60

Pro Gly Glu Arg Lys Ala Arg Asp Cys Thr Val Asn Gly Asp Glu Pro
 65                  70                  75                  80

Asp Cys Val Pro Cys Gln Glu Gly Lys Glu Tyr Thr Asp Lys Ala His
             85                  90                  95

Phe Ser Ser Lys Cys Arg Arg Cys Arg Leu Cys Asp Glu Gly His Gly
            100                 105                 110

Leu Glu Val Glu Ile Asn Cys Thr Arg Thr Gln Asn Thr Lys Cys Arg
        115                 120                 125

Cys Lys Pro Asn Phe Phe Cys Asn Ser Thr Val Cys Glu His Cys Asp
130                 135                 140

Pro Cys Thr Lys Cys Glu His Gly Ile Ile Lys Glu Cys Thr Leu Thr
145                 150                 155                 160

Ser Asn Thr Lys Cys Lys Glu Glu Gly Ser Gly Ser Ser Gly Ser
                165                 170                 175

Ser Gly Ser Gly Leu Pro Asp Val Ala Ser Leu Arg Gln Gln Val Glu
            180                 185                 190

Ala Leu Gln Gly Gln Val Gln His Leu Gln Ala Ala Phe Ser Gln Tyr
        195                 200                 205

Lys Lys Val Glu Leu Phe Pro Asn Gly Gln Ser Val Gly Glu Lys Ile
210                 215                 220

Phe Lys Thr Ala Gly Phe Val Lys Pro Phe Thr Glu Ala Gln Leu Leu
225                 230                 235                 240

Cys Thr Gln Ala Gly Gly Gln Leu Ala Ser Pro Arg Ser Ala Ala Glu
                245                 250                 255

Asn Ala Ala Leu Gln Gln Leu Val Val Ala Lys Asn Glu Ala Ala Phe
            260                 265                 270

Leu Ser Met Thr Asp Ser Lys Thr Glu Gly Lys Phe Thr Tyr Pro Thr
        275                 280                 285

Gly Glu Ser Leu Val Tyr Ser Asn Trp Ala Pro Gly Glu Pro Asn Asp
290                 295                 300

Asp Gly Gly Ser Glu Asp Cys Val Glu Ile Phe Thr Asn Gly Lys Trp
305                 310                 315                 320

Asn Asp Arg Ala Cys Gly Glu Lys Arg Leu Val Val Cys Glu Phe Gly
                325                 330                 335

Gly Ser Pro Ser Ser Ser Ser Ser Ala Trp Ser His Pro Gln Phe
            340                 345                 350

Glu Lys

<210> SEQ ID NO 39
<211> LENGTH: 725
<212> TYPE: DNA
<213> ORGANISM: Artificial
<220> FEATURE:
<223> OTHER INFORMATION: SPN-hs95R-DT4-HtSt

<400> SEQUENCE: 39
aagctttagg gataacaggg taatagccgc caccatggtg gcatctgga ccctgctgcc      60 tctggtgctg acctctgtgg ccagactgtc ctccaagtcc gtgaacgccc aggtgaccga     120
catcaactcc aagggcctgg agctgagaaa gaccgtgacc accgtggaga cccagaacct     180
ggagggcctg caccacgatg gccagttctg ccacaagcct tgtcctcccg gcgagagaaa     240
ggccagagac tgtaccgtga acggcgacga gcctgactgt gtgccttgtc aggagggcaa     300

```
ggagtacacc gacaaggccc acttctcctc caagtgccgg aggtgtaggc tgtgtgatga    360
gggccacggc ctggaggtgg agatcaactg tacccggacc cagaacacca agtgccgctg    420
taagcccaac ttcttctgta actccaccgt gtgtgagcac tgtgacccct gtaccaagtg    480
tgagcacggc atcatcaagg agtgtaccct gacctccaat accaagtgta aggaggaggg    540
atccggctac atcccagaag cacccagaga cggtcaggct tatgtccgca agacggaga    600 atgggttctg ctctcgacct tcttgtcggg tccgagctca agctcatctc atcatcatca    660
tcatcatagc gcttggtctc acccgcagtt cgagaaatga caccatagtg ataagtagcg    720
gccgc                                                                725
```

<210> SEQ ID NO 40
<211> LENGTH: 221
<212> TYPE: PRT
<213> ORGANISM: Artificial
<220> FEATURE:
<223> OTHER INFORMATION: SPN-hs95R-DT4-HtSt

<400> SEQUENCE: 40

```
Met Val Gly Ile Trp Thr Leu Leu Pro Leu Val Leu Thr Ser Val Ala
1               5                   10                  15

Arg Leu Ser Ser Lys Ser Val Asn Ala Gln Val Thr Asp Ile Asn Ser
            20                  25                  30

Lys Gly Leu Glu Leu Arg Lys Thr Val Thr Thr Val Glu Thr Gln Asn
        35                  40                  45

Leu Glu Gly Leu His His Asp Gly Gln Phe Cys His Lys Pro Cys Pro
    50                  55                  60

Pro Gly Glu Arg Lys Ala Arg Asp Cys Thr Val Asn Gly Asp Glu Pro
65                  70                  75                  80

Asp Cys Val Pro Cys Gln Glu Gly Lys Glu Tyr Thr Asp Lys Ala His
                85                  90                  95

Phe Ser Ser Lys Cys Arg Arg Cys Arg Leu Cys Asp Glu Gly His Gly
            100                 105                 110

Leu Glu Val Glu Ile Asn Cys Thr Arg Thr Gln Asn Thr Lys Cys Arg
        115                 120                 125

Cys Lys Pro Asn Phe Phe Cys Asn Ser Thr Val Cys Glu His Cys Asp
    130                 135                 140

Pro Cys Thr Lys Cys Glu His Gly Ile Ile Lys Glu Cys Thr Leu Thr
145                 150                 155                 160

Ser Asn Thr Lys Cys Lys Glu Glu Gly Ser Gly Tyr Ile Pro Glu Ala
                165                 170                 175

Pro Arg Asp Gly Gln Ala Tyr Val Arg Lys Asp Gly Glu Trp Val Leu
            180                 185                 190

Leu Ser Thr Phe Leu Ser Gly Pro Ser Ser Ser Ser His His His
        195                 200                 205

His His His Ser Ala Trp Ser His Pro Gln Phe Glu Lys
    210                 215                 220
```

<210> SEQ ID NO 41
<211> LENGTH: 6
<212> TYPE: PRT
<213> ORGANISM: Artificial
<220> FEATURE:
<223> OTHER INFORMATION: linker
<220> FEATURE:
<221> NAME/KEY: REPEAT
<222> LOCATION: (1)..(3)
<223> OTHER INFORMATION: 0, 1, 2, 3, 4 or 5 repeats

```
<400> SEQUENCE: 41

Gly Ser Ser Gly Ser Gly
1               5

<210> SEQ ID NO 42
<211> LENGTH: 6
<212> TYPE: PRT
<213> ORGANISM: Artificial
<220> FEATURE:
<223> OTHER INFORMATION: linker
<220> FEATURE:
<221> NAME/KEY: REPEAT
<222> LOCATION: (1)..(3)
<223> OTHER INFORMATION: 0, 1, 2, 3, 4 or 5 repeats
<220> FEATURE:
<221> NAME/KEY: REPEAT
<222> LOCATION: (4)..(6)
<223> OTHER INFORMATION: 0, 1, 2, 3, 4 or 5 repeats

<400> SEQUENCE: 42

Gly Thr Thr Gly Thr Gly
1               5

<210> SEQ ID NO 43
<211> LENGTH: 27
<212> TYPE: PRT
<213> ORGANISM: Enterobacteria phage T4

<400> SEQUENCE: 43

Gly Tyr Ile Pro Glu Ala Pro Arg Asp Gly Gln Ala Tyr Val Arg Lys
1               5                   10                  15

Asp Gly Glu Trp Val Leu Leu Ser Thr Phe Leu
            20                  25

<210> SEQ ID NO 44
<211> LENGTH: 27
<212> TYPE: PRT
<213> ORGANISM: Enterobacteria phage RB32

<400> SEQUENCE: 44

Gly Tyr Ile Pro Glu Ala Pro Lys Asp Gly Gln Ala Tyr Val Arg Lys
1               5                   10                  15

Asp Gly Glu Trp Val Leu Leu Ser Thr Phe Leu
            20                  25

<210> SEQ ID NO 45
<211> LENGTH: 26
<212> TYPE: PRT
<213> ORGANISM: Enterobacteria phage RB69

<400> SEQUENCE: 45

Gly Tyr Ile Glu Asp Ala Pro Ser Asp Gly Lys Phe Tyr Val Arg Lys
1               5                   10                  15

Asp Gly Ala Trp Val Glu Leu Pro Thr Ala
            20                  25

<210> SEQ ID NO 46
<211> LENGTH: 27
<212> TYPE: PRT
<213> ORGANISM: Geobacter bemidjiensis Bem

<400> SEQUENCE: 46

Gly Ala Val Gly Asp Ala Pro Lys Asp Gly Lys Leu Tyr Val Arg Gln
1               5                   10                  15

Asn Gly Arg Trp Val Glu Leu Val Thr Ala Ala
```

-continued

```
            20                  25

<210> SEQ ID NO 47
<211> LENGTH: 27
<212> TYPE: PRT
<213> ORGANISM: Enterobacteria phage JS98-C3

<400> SEQUENCE: 47

Thr Lys Leu Gly Asp Ala Pro Ala Asp Gly Lys Leu Tyr Gly Arg Lys
1               5                   10                  15

Asp Ala Ala Trp Ala Glu Ile Leu Asp Asp Thr
            20                  25

<210> SEQ ID NO 48
<211> LENGTH: 27
<212> TYPE: PRT
<213> ORGANISM: Enterobacteria phage JS98-C3

<400> SEQUENCE: 48

Arg Pro Pro Val Ala Pro Thr Ala Asp Gly Leu Pro Tyr Val Leu Val
1               5                   10                  15

Asp Asn Ala Trp Val Leu Leu Ser Asp Phe Val
            20                  25

<210> SEQ ID NO 49
<211> LENGTH: 27
<212> TYPE: PRT
<213> ORGANISM: Enterobacteria phage JS98

<400> SEQUENCE: 49

Gly Lys Leu Gly Asp Ala Pro Ser Asp Gly Lys Leu Tyr Ala Arg Arg
1               5                   10                  15

Asn Ala Ala Trp Ala Glu Val Val Asn Asn Ser
            20                  25

<210> SEQ ID NO 50
<211> LENGTH: 27
<212> TYPE: PRT
<213> ORGANISM: Vibrio phage KVP40

<400> SEQUENCE: 50

Ser Ala Val Pro Glu Ser Pro Asn Asp Gly Gln Leu Tyr Gly Arg Arg
1               5                   10                  15

Asn Ala Thr Trp Glu Leu Ile Ala Leu Ser Asp
            20                  25

<210> SEQ ID NO 51
<211> LENGTH: 27
<212> TYPE: PRT
<213> ORGANISM: Vibrio phage KVP40

<400> SEQUENCE: 51

Asp Gly Val Leu Glu Ala Pro Ala Asp Gly Gln Glu Tyr Val Arg Lys
1               5                   10                  15

Asp Phe Gln Trp Val Leu Pro Thr Tyr Pro Thr
            20                  25

<210> SEQ ID NO 52
<211> LENGTH: 27
<212> TYPE: PRT
<213> ORGANISM: Burkholderia phage BcepNazgul

<400> SEQUENCE: 52
```

```
Gly Gly Ile Pro Asp Ala Pro Ser Asp Gly Val Gly Tyr Ala Arg Lys
1               5                   10                  15

Asp Gly Gly Trp Thr Pro Val Ala Thr Gly Ser
            20                  25

<210> SEQ ID NO 53
<211> LENGTH: 27
<212> TYPE: PRT
<213> ORGANISM: Burkholderia phage BcepNazgul

<400> SEQUENCE: 53

Ser Gly Ile Pro Glu Ala Pro Ala Asp Gly Lys Gln Tyr Ala Arg Lys
1               5                   10                  15

Asn Ser Gly Trp Ala Glu Val Gln Ile Pro Ala
            20                  25

<210> SEQ ID NO 54
<211> LENGTH: 27
<212> TYPE: PRT
<213> ORGANISM: Aeromonas phage Aeh1

<400> SEQUENCE: 54

Thr Ser Ala Phe Asp Val Pro Thr Asp Asp Lys Arg Tyr Ser Arg Arg
1               5                   10                  15

Asn Gly Lys Trp Ile Gln Ser Tyr Tyr Tyr Gly
            20                  25

<210> SEQ ID NO 55
<211> LENGTH: 27
<212> TYPE: PRT
<213> ORGANISM: Aeromonas phage Aeh1

<400> SEQUENCE: 55

His Asp Gly Leu Asp Ala Pro Lys Asp Ala Met Tyr Ala Arg Lys
1               5                   10                  15

Asn Gly Val Trp Thr Ala Phe Asn Pro Gly Gly
            20                  25

<210> SEQ ID NO 56
<211> LENGTH: 26
<212> TYPE: PRT
<213> ORGANISM: Phage MP22

<400> SEQUENCE: 56

Gly Gly Met Ser Asp Ala Pro Ser Asp Gly Ser Asn Tyr Ala Arg Asn
1               5                   10                  15

Asn Gly Ala Trp Gly Lys Leu Gly Thr Ala
            20                  25

<210> SEQ ID NO 57
<211> LENGTH: 27
<212> TYPE: PRT
<213> ORGANISM: Pseudomonas phage DMS3

<400> SEQUENCE: 57

Gly Gly Met Ala Asp Ala Pro Ser Asp Gly Lys Arg Tyr Ala Arg Leu
1               5                   10                  15

Asn Asn Ala Trp Ala Gly Leu Gly Thr Ala Ala
            20                  25

<210> SEQ ID NO 58
<211> LENGTH: 27
<212> TYPE: PRT
```

<213> ORGANISM: Enterobacteria phage RB49

<400> SEQUENCE: 58

Asn Lys Val Asp Asp Val Pro Asp Asp Gly Phe His Tyr Leu Arg Lys
1               5                   10                  15

Arg Gly Glu Trp Val Gln Val Ala Tyr Ala Ala
            20                  25

<210> SEQ ID NO 59
<211> LENGTH: 375
<212> TYPE: PRT
<213> ORGANISM: Homo sapiens
<220> FEATURE:
<221> NAME/KEY: MISC_FEATURE
<223> OTHER INFORMATION: SP-D

<400> SEQUENCE: 59

Met Leu Leu Phe Leu Leu Ser Ala Leu Val Leu Leu Thr Gln Pro Leu
1               5                   10                  15

Gly Tyr Leu Glu Ala Glu Met Lys Thr Tyr Ser His Arg Thr Thr Pro
            20                  25                  30

Ser Ala Cys Thr Leu Val Met Cys Ser Ser Val Glu Ser Gly Leu Pro
        35                  40                  45

Gly Arg Asp Gly Arg Asp Gly Arg Glu Gly Pro Arg Gly Glu Lys Gly
    50                  55                  60

Asp Pro Gly Leu Pro Gly Ala Ala Gly Gln Ala Gly Met Pro Gly Gln
65                  70                  75                  80

Ala Gly Pro Val Gly Pro Lys Gly Asp Asn Gly Ser Val Gly Glu Pro
                85                  90                  95

Gly Pro Lys Gly Asp Thr Gly Pro Ser Gly Pro Pro Gly Pro Pro Gly
            100                 105                 110

Val Pro Gly Pro Ala Gly Arg Glu Gly Pro Leu Gly Lys Gln Gly Asn
        115                 120                 125

Ile Gly Pro Gln Gly Lys Pro Gly Pro Lys Gly Glu Ala Gly Pro Lys
    130                 135                 140

Gly Glu Val Gly Ala Pro Gly Met Gln Gly Ser Ala Gly Ala Arg Gly
145                 150                 155                 160

Leu Ala Gly Pro Lys Gly Glu Arg Gly Val Pro Gly Glu Arg Gly Val
                165                 170                 175

Pro Gly Asn Ala Gly Ala Ala Gly Ser Ala Gly Ala Met Gly Pro Gln
            180                 185                 190

Gly Ser Pro Gly Ala Arg Gly Pro Pro Gly Leu Lys Gly Asp Lys Gly
        195                 200                 205

Ile Pro Gly Asp Lys Gly Ala Lys Gly Glu Ser Gly Leu Pro Asp Val
    210                 215                 220

Ala Ser Leu Arg Gln Gln Val Glu Ala Leu Gln Gly Gln Val Gln His
225                 230                 235                 240

Leu Gln Ala Ala Phe Ser Gln Tyr Lys Lys Val Glu Leu Phe Pro Asn
                245                 250                 255

Gly Gln Ser Val Gly Glu Lys Ile Phe Lys Thr Ala Gly Phe Val Lys
            260                 265                 270

Pro Phe Thr Glu Ala Gln Leu Leu Cys Thr Gln Ala Gly Gly Gln Leu
        275                 280                 285

Ala Ser Pro Arg Ser Ala Ala Glu Asn Ala Leu Gln Gln Leu Val
    290                 295                 300

Val Ala Lys Asn Glu Ala Ala Phe Leu Ser Met Thr Asp Ser Lys Thr
305                 310                 315                 320

```
Glu Gly Lys Phe Thr Tyr Pro Thr Gly Glu Ser Leu Val Tyr Ser Asn
                325                 330                 335

Trp Ala Pro Gly Glu Pro Asn Asp Asp Gly Gly Ser Glu Asp Cys Val
            340                 345                 350

Glu Ile Phe Thr Asn Gly Lys Trp Asn Asp Arg Ala Cys Gly Glu Lys
                355                 360                 365

Arg Leu Val Val Cys Glu Phe
            370                 375

<210> SEQ ID NO 60
<211> LENGTH: 271
<212> TYPE: PRT
<213> ORGANISM: Homo sapiens
<220> FEATURE:
<221> NAME/KEY: MISC_FEATURE
<223> OTHER INFORMATION: collectin-11

<400> SEQUENCE: 60

Met Arg Gly Asn Leu Ala Leu Val Gly Val Leu Ile Ser Leu Ala Phe
1               5                   10                  15

Leu Ser Leu Leu Pro Ser Gly His Pro Gln Pro Ala Gly Asp Asp Ala
                20                  25                  30

Cys Ser Val Gln Ile Leu Val Pro Gly Leu Lys Gly Asp Ala Gly Glu
            35                  40                  45

Lys Gly Asp Lys Gly Ala Pro Gly Arg Pro Gly Arg Val Gly Pro Thr
    50                  55                  60

Gly Glu Lys Gly Asp Met Gly Asp Lys Gly Gln Lys Gly Ser Val Gly
65                  70                  75                  80

Arg His Gly Lys Ile Gly Pro Ile Gly Ser Lys Gly Glu Lys Gly Asp
                85                  90                  95

Ser Gly Asp Ile Gly Pro Pro Gly Pro Asn Gly Glu Pro Gly Leu Pro
            100                 105                 110

Cys Glu Cys Ser Gln Leu Arg Lys Ala Ile Gly Glu Met Asp Asn Gln
        115                 120                 125

Val Ser Gln Leu Thr Ser Glu Leu Lys Phe Ile Lys Asn Ala Val Ala
    130                 135                 140

Gly Val Arg Glu Thr Glu Ser Lys Ile Tyr Leu Leu Val Lys Glu Glu
145                 150                 155                 160

Lys Arg Tyr Ala Asp Ala Gln Leu Ser Cys Gln Gly Arg Gly Gly Thr
                165                 170                 175

Leu Ser Met Pro Lys Asp Glu Ala Ala Asn Gly Leu Met Ala Ala Tyr
            180                 185                 190

Leu Ala Gln Ala Gly Leu Ala Arg Val Phe Ile Gly Ile Asn Asp Leu
        195                 200                 205

Glu Lys Glu Gly Ala Phe Val Tyr Ser Asp His Ser Pro Met Arg Thr
    210                 215                 220

Phe Asn Lys Trp Arg Ser Gly Glu Pro Asn Asn Ala Tyr Asp Glu Glu
225                 230                 235                 240

Asp Cys Val Glu Met Val Ala Ser Gly Gly Trp Asn Asp Val Ala Cys
                245                 250                 255

His Thr Thr Met Tyr Phe Met Cys Glu Phe Asp Lys Glu Asn Met
            260                 265                 270

<210> SEQ ID NO 61
<211> LENGTH: 30
<212> TYPE: PRT
<213> ORGANISM: Homo sapiens
```

-continued

```
<220> FEATURE:
<221> NAME/KEY: MISC_FEATURE
<223> OTHER INFORMATION: tenascin

<400> SEQUENCE: 61

Ala Cys Gly Cys Ala Ala Ala Pro Asp Val Lys Glu Leu Leu Ser Arg
1               5                   10                  15

Leu Glu Glu Leu Glu Asn Leu Val Ser Ser Leu Arg Glu Gln
            20                  25                  30
```

MULTIMERIC TNF RECEPTOR FUSION PROTEINS AND NUCLEIC ACIDS ENCODING SAME

This application is a National Stage of International Application PCT/EP2009/057396, filed Jun. 15, 2009, published Jan. 14, 2010, under PCT Article 21(2) in English; which claims the priority of EP 08010978.8, filed Jun. 17, 2008; the contents of the above applications are incorporated herein by reference in their entirety.

REFERENCE TO SEQUENCE LISTING, TABLE OR COMPUTER PROGRAM

The Sequence Listing is concurrently submitted herewith with the specification as an ASCII formatted text file via EFS-Web with a file name of Sequence_Listing.txt with a creation date of Dec. 16, 2010, and a size of 124 kilobytes. The Sequence Listing filed via EFS-Web is part of the specification and is hereby incorporated in its entirety by reference herein.

The present invention refers to fusion proteins comprising a TNF receptor family extracellular domain fused to a trimerization domain, and a nucleic acid molecule encoding the fusion protein. The fusion protein may be present as a trimeric complex. It is suitable for therapeutic, diagnostic and/or research applications.

Trimeric fusion proteins comprising the extracellular domain of a TNF family receptor and a Fc immunoglobulin domain are known (e.g. WO 95/27735). This fusion protein is suitable for the treatment of autoimmune disorders, Graft-versus-Host disease, stroke, myocardial infarction or paraplegia.

It was an object of the present invention to provide novel agents based on TNF family receptor extracellular domains having improved pharmaceutical properties.

Thus, the present invention relates to a fusion protein comprising
  (i) a TNF family receptor extracellular domain or at least the ligand binding domain thereof,
  (ii) a flexible linker element between components (i) and (iii), and
  (iii) a trimerization domain, particularly selected from a bacteriophage foldon, e.g. T4 or RB69 foldon domain, a bacterial foldon domain, e.g. *Geobacter bemidjiensis* foldon, from a collectin, e.g. from the Surfactant Protein D (SP-D) or collectin-11, or from a tenascin (TNC).

The fusion protein may be a monomeric protein or a trimeric protein. Preferably, the fusion protein is present as a trimeric complex consisting of three identical monomeric units. The trimeric complex may be associated by non-covalent and/or covalent interactions mediated by the trimerization domain. Additionally, the trimeric complex may be stabilized by chemical crosslinking, e.g. via a homo- or hetero-multifunctional linker such as bis(sulfosuccinimidyl) suberate.

Component (i) of the fusion protein is an extracellular binding domain of a TNF family receptor. Preferably, component (i) is a mammalian, particularly human, TNF family receptor extracellular domain including allelic variants and/or derivatives thereof. The TNF family receptor may be e.g. selected from TNFRSF1a (TNFR1; SEQ ID NO: 1, preferably at least Leu30-Glu200), TNFRSF1b (TNF-R-II; SEQ ID NO: 2, preferably at least Leu23-Ser204), TNFRSF3 (LTBR; SEQ ID NO: 3, preferably at least Ser28-Gly223), TNFRSF4 (SEQ ID NO: 4, preferably at least Leu29-Asp170), TNFRSF5 (CD40; SEQ ID NO: 5, preferably at least Glu21-Arg191), TNFRSF6 (CD95R, FAS; SEQ ID NO: 6, preferably at least Arg17-Glu168), TNFRSF6b (SEQ ID NO: 7, preferably at least Val30-Ala214), TNFRSF7 (SEQ ID NO: 8, preferably at least Thr21-Ser127), TNFRSF8 (SEQ ID NO: 9, preferably at least Phe19-Thr173 or at least Asp224-Gly385), TNFRSF9 (SEQ ID NO: 10, preferably at least Leu24-Ser145), TNFRSF10a (SEQ ID NO: 11, preferably at least Glu130-Ser234), TNFRSF10b (SEQ ID NO: 12, preferably at least Glu78-Gly184), TNFRSF10c (SEQ ID NO: 13, preferably at least Gly50-Ala155), TNFRSF10d (SEQ ID NO: 14, preferably at least Glu80-Ser184), TNFRSF11a (RANK; SEQ ID NO: 15, preferably at least Leu28-Ser197), TNFRSF11b (OPG; SEQ ID NO: 16, preferably at least Glu21-Ala205), TNFRSF12a (SEQ ID NO: 17, preferably at least Glu28-Ala70), TNFRSF13b (TACI; SEQ ID NO: 18, preferably at least Ser68-Ser110), TNFRSF13c (BAFF-R; SEQ ID NO: 19, preferably at least Asp13-Glu69), TNFRSF14 (SEQ ID NO: 20, preferably at least Leu39-Ser145), TNFRSF16 (NGFR; SEQ ID NO: 21, preferably at least Glu29-Glu190), TNFRSF17 (BCMA; SEQ ID NO: 22, preferably at least Ala5-Gly51), TNFRSF18-var1 (SEQ ID NO: 23, preferably at least Gln26-Gly138), TNFRSF18-var2 (SEQ ID NO: 24, preferably at least Gln26-Ser255), TNFRSF19 (SEQ ID NO: 25, preferably at least Lys26-Gly139), TNFRSF19L (SEQ ID NO: 26, preferably at least Thr25-Gly125), TNFRSF21 (SEQ ID NO: 27, preferably at least Gln42; Gln63-Ser218), TNFRSF25-var1 (SEQ ID NO: 28, preferably at least Gln25-Thr181), TNFRSF25-var2 (SEQ ID NO: 29, preferably at least Gln25-Gly196), TNFRSF25-var3 (SEQ ID NO: 30, preferably at least Gln25-Thr181), TNFRSF25-var4 (SEQ ID NO: 31, preferably at least Gln25-Gln151), and TNFRSF27 (EDA2R; SEQ ID NO: 32, preferably at least Asp2-Ser123) (FIG. 6). The structure of these receptors and the location of the extracellular domains thereof is described in a review article by Wajant et al. (2003), Essays in Biochemistry 39, 53-71, the content of which is herein incorporated by reference. A variety of fragments comprising all or a portion of the TNF receptor extracellular domain (including the ligand-binding domain) can be used for the production of trimeric TNFR-SF proteins. Preferred regions for the production of trimeric TNFR-SF proteins are referred to in FIG. 6.

A schematic picture of the domain structure of CD95R (Fas) according to Wajant et al. (2003), supra, is shown in FIG. 1. The numbering refers to the mature protein. L means the secretory signal sequence, CRD a cysteine-rich domain, TM a transmembrane domain and PLAD a pre-ligand binding assembly domain. In an especially preferred embodiment, component (i) of the recombinant fusion protein is selected from the extracellular domain of human CD95 receptor comprising amino acids 1 to 169 of the mature CD95R protein.

Component (ii) is a flexible linker element located between components (i) and The flexible linker element preferably has a length of 3-20 amino acids, particularly a length of 5, 6, 9, 12, 15 or 18 amino acids. The linker element is preferably a glycine/serine linker, i.e. a peptide linker substantially consisting of the amino acids glycine and serine. In an especially preferred embodiment, the linker has an amino acid sequence selected from $(GSS)_a (GSG)_b$ (SEQ ID NO: 41) and $(GTT)_a (GTG)_b$ (SEQ ID NO: 42) wherein a or b is 0, 1, 2, 3, 4 or 5, wherein when a=0 then b is ≥1 and when b=0 then a is ≥1. It is evident for the skilled person that in cases in which the TNF family receptor extracellular domain or the ligand binding domain thereof already terminates with a G, such a G may form the first G of the linker in the linker sequence. It is also evident for the skilled person that in cases in which the trimerization domain already starts with a G, such a G may form the last G of the linker in the linker sequence.

Component (iii) is a trimerization domain. Preferably, component (iii) is a bacteriophage fibritin trimerization domain, a fibritin related trimerization domain from geobacteraceae or a collectin domain. In a preferred embodiment, component (iii) is a fibritin trimerization domain from bacteriophage T4 or related bacteriophages such as T-even bacteriophages or phage RB69 or phage AR1. The T4 fibritin trimerization domain is e.g. described in U.S. Pat. No. 6,911, 205 or WO 01/19958, the contents of which is herein incorporated by reference.

More preferably, component (iii) comprises the amino acid sequence (a) (G)YIPEAPRDGQ AYVRKDGEWV LLSTFL (SEQ ID NO: 43), (b) (G)YIPEAPKDGQ AYVRKDGEWV LL STFL (SEQ ID NO: 44), (c) (G)YIEDAPSDGK FYVRKDGAWV ELPTA (SEQ ID NO: 45), (d) GAVGDAPKDG KLYVRQNGRW VELVTAA (SEQ ID NO: 46), (e) TKLGDAPADG KLYG RKDAAW AEILDDT (SEQ ID NO: 47), (f) RPPVAPTADG LPYVLVDNAW VLLSDFV (SEQ ID NO: 48), (g) GKLGDAPSDG KLYARRNAAW AEVVNNS (SEQ ID NO: 49), (h) SAVPESPNDG QLYGRRNATW ELIALSD (SEQ ID NO: 50), (i) DGVLEAPADG QEYVRKDFQW VLPTYPT (SEQ ID NO: 51), (j) GGIPDAPSDG VGYARKDGGW TPVATGS (SEQ ID NO: 52), (k) SGIPEAPADG KQYARKNSGW AEVQ IPA (SEQ ID NO: 53), (l) TSAFDVPTDD KRYSRRNGKW IQSYYYG (SEQ ID NO: 54), (m) HDGLDAPKDD AMYARKNGVW TAFNPG G (SEQ ID NO: 55), (n) GGMSDAPSDG SNYARNNGAW GKL GTA (SEQ ID NO: 56), (o) GGMADAPSDG KRYARLNNAW AGLGTAA (SEQ ID NO: 57), (p) NKVDDVPDDG FHYL RKRGEW VQVAYAA (SEQ ID NO: 58), or a sequence variant having an identity of at least 70%, 75%, 80%, 85% or preferably of at least 90% thereto. Examples of preferred sequence variants of (a) and (c) are shown in in PCT/EP20 07/007517, the content of which is herein incorporated by reference. In this embodiment, it is preferred that component (iii) has a length of from 20 up to 30 amino acids.

In a further preferred embodiment, component (iii) comprises a trimerization domain from a collectin, particularly a human collectin, which comprises a coiled-coil motif, e.g. from a lung surfactant protein D (SP-D), in addition to a further sequence from said collectin of at least, 20, 50, 70, 80, 90, 100, 110, 115, 120 amino acids, e.g. the entire C-terminal domain. Such a trimerization domain may e.g. comprise amino acids Leu222-Phe375 from human SP-D. Further suitable collectin domains are described in EP 07 013 506.6, the content of which is herein incorporated by reference.

In a further preferred embodiment, the collectin trimerization domain (iii) may comprise any collectin family member. Such members and their structures are summarized in, e.g., Hakansson et al. (Protein Science, 2000, 9:1607-1617) and may comprise surfactant protein-D, surfactant protein-A, mannan-binding protein-A, mannan-binding-protein-C, collectin liver 1, collectin placenta 1, or collectin-11. The collectin trimerization domain as described herein may be from a different species than the TNF family receptor extracellular domain or the ligand binding domain thereof as described herein. Alternatively, the collectin trimerization domain as described herein may be from the same species than the TNF family receptor extracellular domain or the ligand binding domain thereof described herein. In a preferred embodiment, the collectin domain as described herein is from human and the TNF family receptor extracellular domain or the ligand binding domain thereof as described herein is from human. In a preferred embodiment, the collectin trimerization domain comprises the neck and carbohydrate binding domain (CRD) domain of the surfactant protein-D, particularly amino acids 217-375, 218-375, 219-375, 220-375, 221-375, 222-375, 223-375, 224-375, 225-375 from human surfactant protein-D of SEQ ID NO: 59. In another preferred embodiment, the collectin trimerization domain comprises the neck domain of the surfactant protein-D, particularly amino acids 217-257, 218-257, 219-257, 220-257, 221-257, 222-257, 223-257, 224-257, or 225-257 from human surfactant protein-D of SEQ ID NO: 59. In another preferred embodiment, the collectin trimerization domain comprises the neck and carbohydrate binding domain (CRD) domain of collectin-11, particularly amino acids 110-271, 116-271, or 121-271 of human collectin-11 of SEQ ID NO: 60. In another preferred embodiment, the collectin trimerization domain comprises the neck domain of collectin-11, particularly amino acids 110-147, 110-148, 110-149, 110-150, 110-151, 116-147, 116-148, 116-149, 116-150, 116-151, 121-147, 121-148, 121-149, 121-150, or 121-151 of human collectin-11 of SEQ ID NO: 60.

The collectin trimerization domain (iii) may comprise a mutant, e.g., a mutant of surfactant protein-D or collectin-11, which does not bind to mannose. Such mutants may be identified by methods known to the skilled person, e.g., the methods disclosed in Crouch et al. (J Biol Chem, 2006, 281(26): 18008-18014). The collectin trimerization domain (iii) may further comprise a mutant which comprises at least one amino acid substitution as is described herein and may be generated as described herein. Such amino acid substitutions may modify the binding of the collectin trimerization domain to its ligand mannose and lead to an alteration of the clearance rate of a fusion protein as described herein when used in therapy and/or as pharmaceutical composition. The modification may result in a decreased or no binding to mannose and a low clearance rate. Such modifications may be achieved by, e.g., an amino acid substitution that affects the amino acid position F355 of human surfactant protein-D of SEQ ID NO: 59, particularly by the amino acid substitution F355A, F355S, F355T, F355E, F355D, F355K, or F355R. Alternatively, the modification may result in an increased binding to mannose and a high clearance rate. Such modifications may be achieved by, e.g., an amino acid substitution that affects the amino acid position F355 of human surfactant protein-D of SEQ ID NO: 59, particularly by the amino acid substitution F355L, F355Y, or F355W.

In a further preferred embodiment, the trimerization domain is a tenascin domain comprising the amino acid sequence of SEQ ID NO: 61 or a sequence having an identity of at least 70% thereto as described in EP 07 012 523.2, the content of which is herein incorporated by reference, In another further preferred embodiment the trimerization domain may be artificially glycosylated which may confer enhanced solubility to the protein and may be useful for modulating pharmacokinetics without being limited thereto.

According to the commonly accepted N-glycosylation rule, a tripeptide consensus sequence consisting of N-X-S/T is required for N-glycosylation of proteins.

In a preferred embodiment a glycosylation site may be introduced by mutation of any of the sequences of SEQ ID NO: 49 to SEQ ID NO: 58 or a sequence variant having an identity of at least 70%, 75%, 80%, 85% or preferably of at least 90% thereto. The mutation preferably comprises a substitution mutation of one or more amino acids at positions 7-12, preferably at positions 8-11 of the sequences to asparagine (N), serine (S) or threonine (T) in order to obtain a glycosylation site. It is particularly preferred that the mutation comprises a substitution mutation of the amino acid at position 8 and/or 9 to asparagine and/or a mutation of the amino acid at position 10 and/or 11 to either serine or threonine.

Amino acid positions 8-10, 9-11 and 10-12 are particularly suitable for the introduction of the tripeptide motif N-X-S/T in order to obtain a glycosylation site.

In the fusion protein of the invention, it is preferred that component (i) is located N-terminally and component (iii) is located C-terminally. The invention, however, also refers to embodiments, wherein component (iii) is located N-terminally and component (i) is located C-terminally.

The fusion protein may additionally comprise an N-terminal signal peptide domain, which allows processing, e.g. extracellular secretion, in a suitable host cell. Preferably, the N-terminal signal peptide domain comprises a protease, e.g. a signal peptidase cleavage site and thus may be removed after or during expression to obtain the mature protein. Further, the fusion protein may additionally comprise a C-terminal flexible element, having a length of e.g. 1-50, preferably 10-30 amino acids which may include or connect to a recognition/purification domain, e.g. a FLAG domain, a Strep-tag domain and/or a poly-His domain.

Figure 2:

FIG. 2 shows a schematic picture of a preferred fusion protein of the present invention comprising an N-terminal signal peptide domain (SP), the extracellular CD95 domain (E-CD95), a flexible linker $(GSS)_3$ GS, a trimerization motif, a further spacer, e.g. a serine spacer for providing a flexibility of purification tag(s) and a tag sequence (St), e.g. the Streptag domain.

A further aspect of the present invention relates to a nucleic acid molecule encoding a fusion protein as described above. The nucleic acid molecule may be a DNA molecule, e.g. a double-stranded or single-stranded DNA molecule, or an RNA molecule. The nucleic acid molecule may encode the fusion protein or a precursor thereof, e.g. a pro- or pre-pro-form of the fusion protein which may comprise a signal sequence or other heterologous amino acid portions for secretion or purification which are preferably located at the N- and/or C-terminus of the fusion protein. The heterologous amino acid portions may be linked to the first and/or second domain via a protease cleavage site, e.g. a Factor $X_a$, thrombin or IgA protease cleavage site.

The nucleic acid molecule may be operatively linked to an expression control sequence, e.g. an expression control sequence which allows expression of the nucleic acid molecule in a desired host cell. The nucleic acid molecule may be located on a vector, e.g. a plasmid, a bacteriophage, a viral vector, a chromasal integration vector, etc. Examples of suitable expression control sequences and vectors are described for example by Sambrook et al, (1989) *Molecular Cloning, A Laboratory Manual*, Cold Spring Harbor Press, and Ausubel et al. (1989), *Current Protocols in Molecular Biology*, John Wiley & Sons or more recent editions thereof.

Various expression vector/host cell systems may be used to express the nucleic acid sequences encoding the fusion proteins of the present invention. Suitable host cells include, but are not limited to, prokaryotic cells such as bacteria, e,g. *E. coli*, eukaryotic host cells such as yeast cells, insect cells, plant cells or animal cells, preferably mammalian cells and, more preferably, human or rodent, e.g. CHO, cells.

Further, the invention relates to a non-human organism transformed or transfected with a nucleic acid molecule as described above. Such transgenic organisms may be generated by known methods of genetic transfer including homologous recombination.

The fusion protein or the nucleic acid coding therefor may be used for pharmaceutical, diagnostic and/or research applications.

A further aspect of the present invention relates to a pharmaceutical or diagnostic composition comprising as an active agent at least one fusion protein or a nucleic acid molecule coding therefor as described above.

In this embodiment of the invention the composition may be used in the prophylaxis and/or treatment of disorders selected from disorders caused by, associated with and/or accompanied by apoptotic processes, autoimmune disorders, e.g. rheumatoid and/or arthritic diseases, degenerative diseases, e.g. neurodegenerative diseases such as multiple sclerosis, injuries of the nervous system, e.g. the central nervous system, including the spinal cord, myocardial infarctions, and heart failure, stroke, and transplant rejections, Graft-versus-host disease (GVHD), and pneumonitis, particularly radiation-induced pneumonitis. Additionally, the composition may be used for the treatment of cancers, preferably solid cancers, e.g. brain cancers, e.g. glioblastomas. Alternatively, the cancer to be treated may be a cancer of lymphoid or myeloid origin.

In another embodiment, the pharmaceutical or diagnostic composition comprising as an active agent at least one fusion protein comprising the extracellular domain of TNFRSF13b (TACI, SEQ ID NO:18) and/or TNFRSF17 (BCMA, SEQ ID NO:22) or a nucleic acid molecule coding therefor is particularly suitable for the treatment of leukaemia and/or diseases associated with hyperproliferation of B cells.

In yet another embodiment, the pharmaceutical or diagnostic composition comprising as an active agent at least a fusion protein comprising the extracellular domain of TNFRSF13c (BAFF-R, SEQ ID NO:19) or a nucleic acid molecule coding therefor is particularly suitable for the treatment of autoimmune disorders and/or leukaemia.

The composition may be administered as monotherapy or as combination therapy with further medicaments, e.g. anti-inflammatory agents such as Etanercept or Enbrel; especially TNF-neutralizing medicaments.

The fusion protein is administered to a subject in need thereof, particularly a human patient, in a sufficient dose for the treatment of the specific conditions by suitable means. For example, the fusion protein may be formulated as a pharmaceutical composition together with pharmaceutically acceptable carriers, diluents and/or adjuvants. Therapeutic efficacy and toxicity may be determined according to standard protocols. The pharmaceutical composition may be administered systemically, e,g. intraperitoneally, intramuscularly or intravenously or locally, e.g. intranasally, subcutaneously or intrathecally. Preferred is intravenous administration.

The dose of the fusion protein administered will of course be dependent on the subject to be treated, on the subject's weight, the type and severity of the disease, the manner of administration and the judgement of the prescribing physician. For the administration of fusion proteins, a daily dose of 0.001 to 100 mg/kg is suitable.

In a further embodiment, the trimerization domain according to the invention or a sequence variant having an identity of at least 70% can be used for fusion to a heterologous protein of interest, particularly a mammalian, e.g. a human protein of interest.

It is preferred that the trimerization domain is located C-terminally of the protein of interest but it is also an aspect of the present invention that the trimerization domain is located N-terminally of the protein of interest.

A further aspect of the present invention is a fusion protein comprising
(i) a protein of interest
(ii) optionally a flexible linker element comprising more than 2 amino acids between components (i) and (iii), and
(iii) a trimerization domain as defined above,
wherein the protein of interest (i) is heterologous to the trimerization domain.

FIGURES

FIG. 1 Schematic picture of the domain structure of CD95R (Fas) according to Wajant et al. (2003). The numbering refers to the mature protein. L means the secretory signal sequence, CRD a cysteine-rich domain, TM a transmembrane domain and PLAD a pre-ligand binding assembly domain.

FIG. 2 Schematic picture of a preferred fusion protein of the present invention comprising an N-terminal signal peptide domain (SP), the extracellular CD95 domain (E-CD95), a flexible linker (GSS)$_3$ GS, a trimerization motif, a further spacer, e.g. a serine spacer for providing a flexibility of purification tag(s) and a tag sequence (St), e.g. the Streptag domain.

Figure 3:
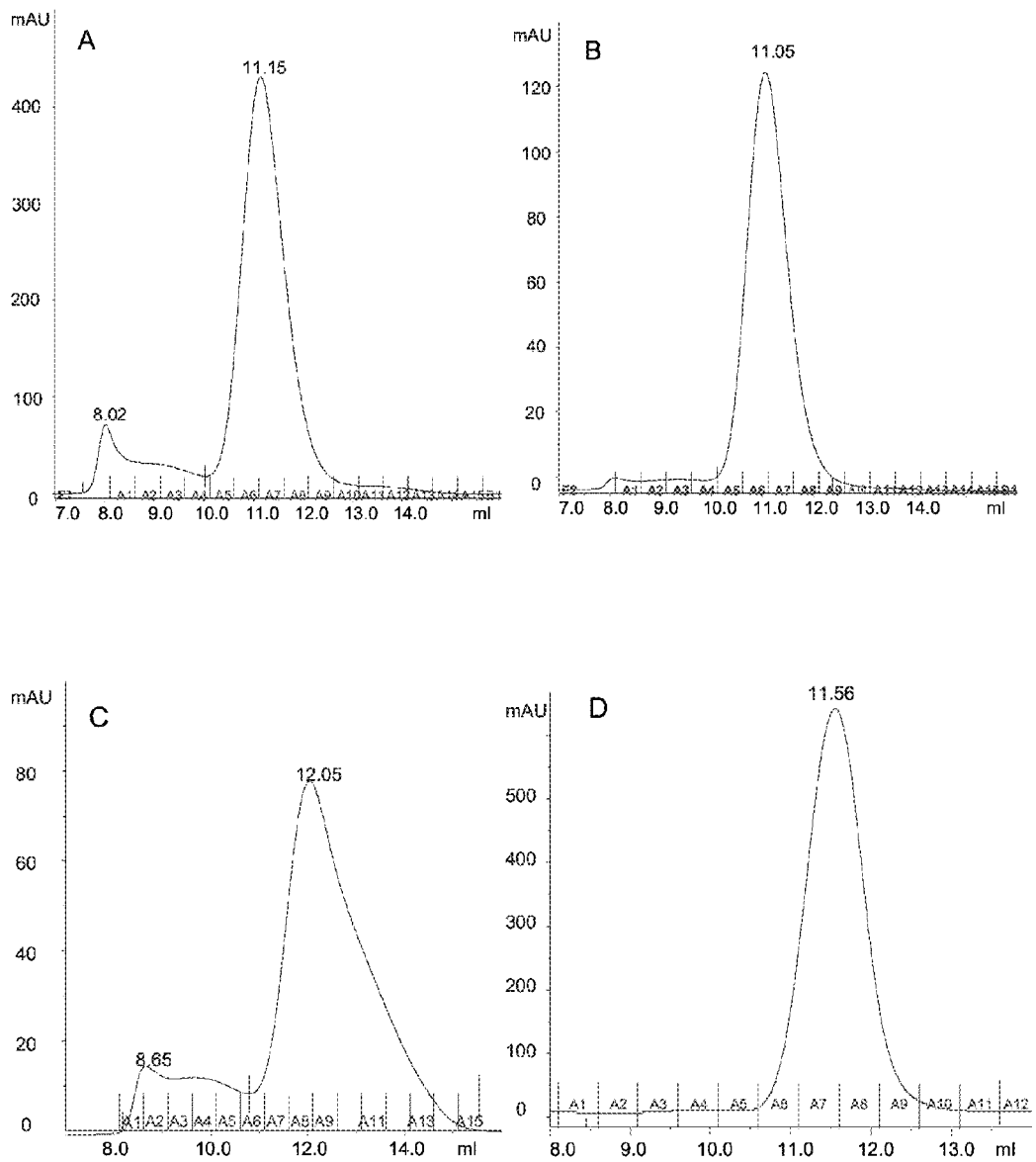

FIG. 3A-3D Elution profiles of SEC chromatograms for the fusion proteins HS95R-A69St (FIG. 3A), HS95R-AT4-St (FIG. 3B), HS95R-ASPD-St (FIG. 3C) and APG101 (FIG. 3D). The individual SEC-runs were performed in different setups with respect to sample amount, loop-volume and calibration.

Figure 4:
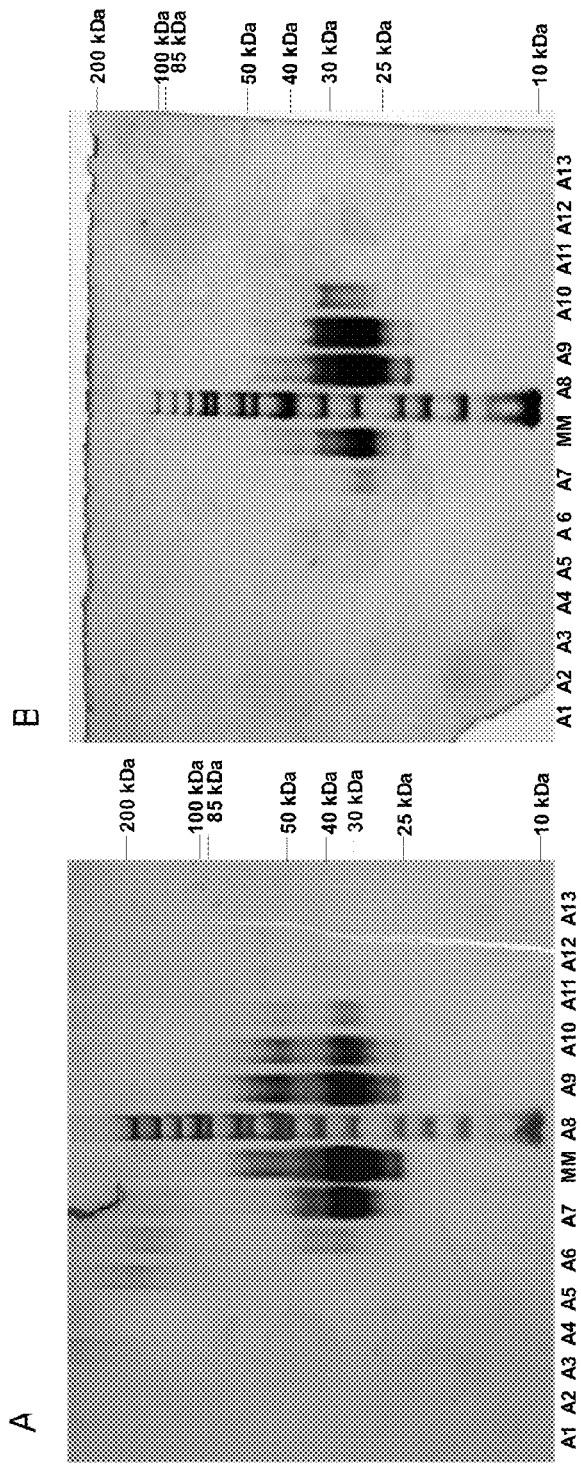
Figure 4:
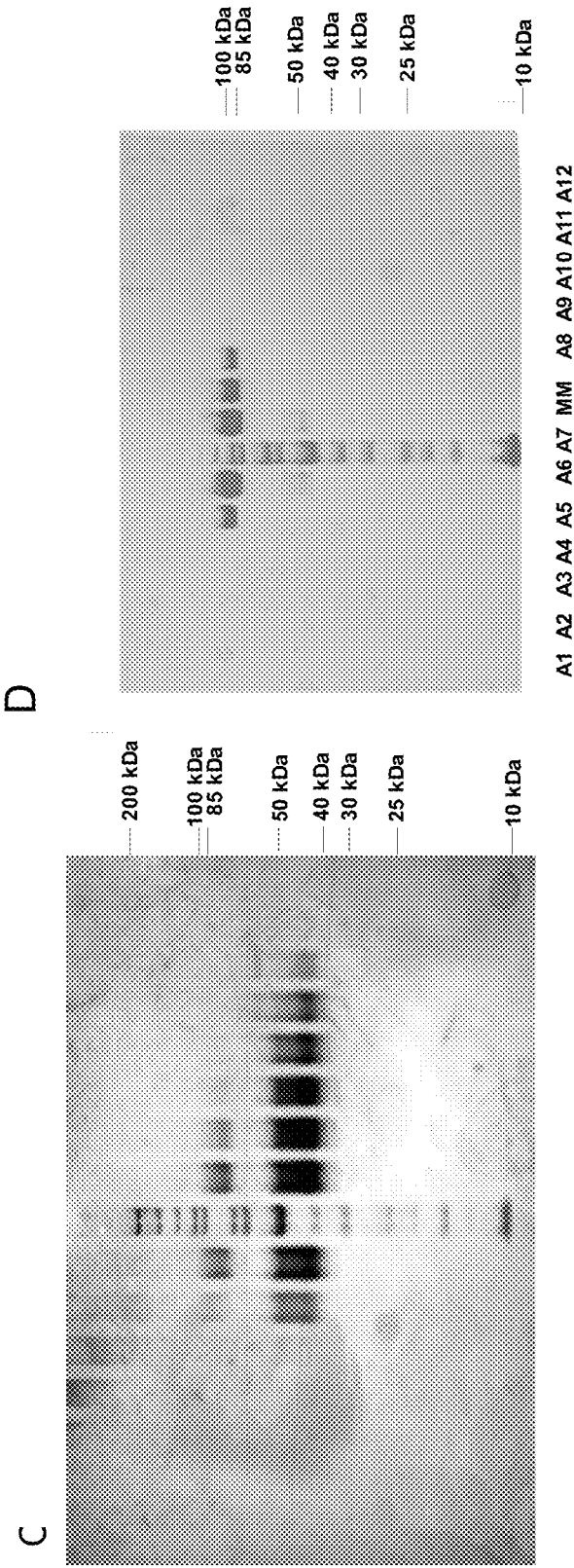

FIG. 4A-4D Results of an SDS-PAGE analysis of the SEC fractions of the trimeric CD95-R fusion proteins HS95R-A69-St (FIG. 4A), HS95R-AT4-St (FIG. 4B) and HS95R-ASPD-St (FIG. 4C) as well as the results of the dimeric CD95R-Fc fusionprotein (APG101, for reference see WO 2004/085478; FIG. 4D) under non-reducing conditions (silver-stain).

Figure 5:
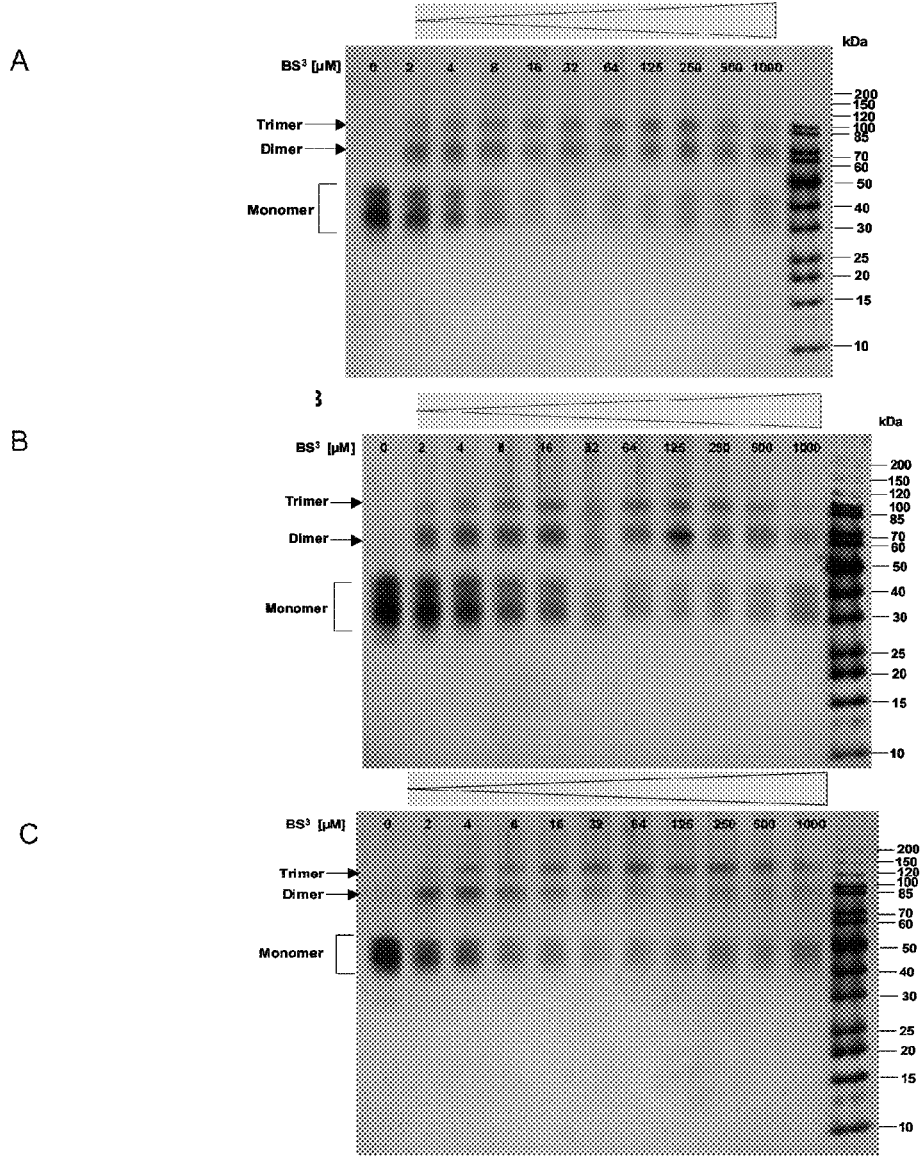
Figure 5:
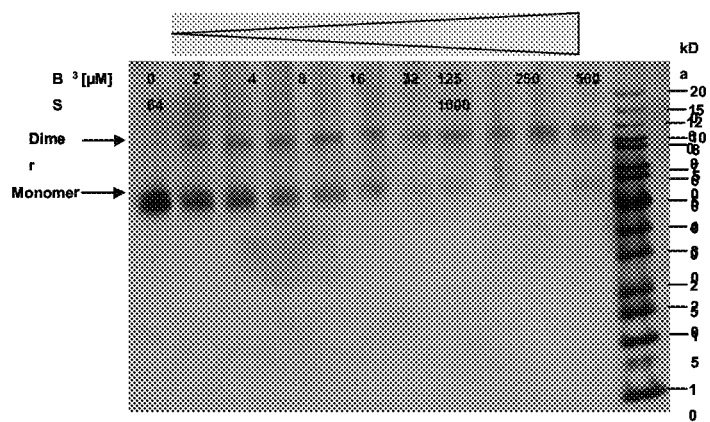

FIG. 5A-5D SDS-PAGE analysis of covalently BS$^3$-crosslinked hs95R-A69-St (FIG. 5A), hs95R-AT4-St (FIG. 5B), hs95R-ASPD-St (FIG. 5C) and the dimeric CD95R-Fc fusionprotein (APG101, FIG. 5D).

FIG. 6A-6C TNFR superfamily proteins, including reference sequences and localization of ligand-binding domains.

EXAMPLE

In the following, the basic structures of recombinant proteins of the invention are shown exemplified for the extracellular domain of the CD95 receptor.

1.1 CD95R-T4 Foldon-Fusion Polypeptide

The nucleic acid sequence coding for this fusion protein and the corresponding amino acid sequence are shown in SEQ ID NOs:33 and 34, respectively.
A) Amino acids Met1-Ala16
   Signal peptide
B) Amino acids Arg17-Glu168
   Extracellular domain of human CD95 receptor
C) Amino acids Gly169-Gly180
   Flexible linker element
D) Amino acids Tyr181-Leu206
   Trimerization domain of the bacteriophage T4-fibritin
E) Amino acids Ser207-Lys224
   Flexible element with Streptag II motif.
The resulting protein was designated hs95R-AT4-St.

1.2 CD95R-RB69 Fusion Polypeptide

The nucleic acid sequence coding for this fusion protein and the corresponding amino acid sequence are shown in SEQ ID NOs:35 and 36, respectively.
A) Amino acids Met1-Ala16
   Signal peptide
B) Amino acids Arg17-Glu168
   Extracellular domain of human CD95 receptor
C) Amino acids Gly169-Gly180
   Flexible linker element
D) Amino acids Tyr181-Ala205
   Trimerization domain of the bacteriophage RB69 fibritin
E) Amino acids Ser206-Lys223
   Flexible element with Streptag II motif.
The resulting protein was designated hs95R-A69-St.

1.3 CD95R-SP-D Fusion Polypeptide

The nucleic acid sequence coding for this fusion protein and the corresponding amino acid sequence are shown in SEQ ID NOs:37 and 38, respectively.
A) Amino acids Met1-Ala16
   Signal peptide
B) Amino acids Arg17-Glu168
   Extracellular domain of human CD95 receptor
C) Amino acids Gly169-Gly180
   Flexible linker element
D) Amino acids Leu181-Phe335
   Trimerization domain of the surfactant protein D
E) Amino acids Gly336-Lys354
   Flexible element with Streptag II motif.
The resulting protein was designated hs95R-ASPD-St.

1.4 CD95R-T4 Foldon Fusion Polypeptides with Shortened Linker

The nucleic acid sequence coding for this fusion protein and the corresponding amino acid sequence are shown in SEQ ID NOs:39 and 40, respectively.
A) Amino acids Met1-Ala16
   Signal peptide
B) Amino acids Arg17-Glu168
   Extracellular domain of human CD95 receptor
C) Amino acids Gly169-Gly171
   Flexible linker element
D) Amino acids Tyr172-Leu197
   Trimerization domain of the bacteriophage T-4 fibritin
E) Amino acids Ser198-Lys221
   Flexible element with hexa-histidin and Streptag II motifs.
The resulting protein was designated hs95R-DT4-HTSt.

Similar constructs with a linker length of eight or five amino acids were also constructed.

Interestingly, a shortened linker of 3 amino acids resulted in a considerably decreased expression rate as compared to longer linkers of more than 3 amino acids.

2. Cloning Strategy

The synthetic DNA fragments encoding the proteins described under section 1 were subcloned into the pcDNA4/HisMax backbone (Invitrogen) using the unique Hind III and Not I sites of the plasmid.

Sequences coding for the C-terminal flexible elements may be deleted if the fusion polypeptides are used for pharmaceutical applications.

3. Expression and Purification 3.1 Expression in Hek 293T Cells

Hek 293T cells were grown in DMEM-F12 medium (Invitrogen) supplemented with 10% FCS, 1% Penstrep, 20 mM Hepes pH 7.4 and 17.5 mM glucose were transiently transfected with a plasmid containing an expression cassette for one of the above-indicated fusion proteins. Transfection was carried out using high molecular weight polyethyleneimine.

3.2 Expression in CHO-K1 Cells

CHO-K1 cells were grown in F12 GlutaMAX (GibCo), 10% FCS, 1% Penstrep, 10 mM Hepes, pH 7.4, and 17.5 mM glucose. The cells were transfected with a plasmid containing an expression cassette for one of the above fusion polypeptides. Transfection was carried out using high molecular weight polyethyleneimine. Stable cell clones were selected prior to protein production, using the phleomycin resistance gene of the pcDNA4-HisMax-backbone.

3.3 Purification

CD95R fusion proteins were affinity purified from cell culture supernatant via Streptactin Sepharose columns (IBA GmbH). Streptactin Sepharose was packed into a column, equilibrated with wash buffer (100 mM TrisHCl, 150 mM NaCl pH 8,0) and the cell culture supernatant was applied to the column.

Subsequently, the column was washed with 15 ml wash buffer and bound fusion protein was eluted stepwise by addition of elution buffer (phosphate buffered saline, 2.5 mM Desthiobiotin pH 7.4). The protein amount of the eluate fractions was quantified and peak fractions were concentrated by ultrafiltration and further purified by size exclusion chromatography (SEC).

SEC was performed on a Superdex 200 column using an Äkta chromatography system (Äkta purifier, GE Healthcare). The column was equilibrated with phosphate buffered saline and the concentrated, Streptactin purified fusion polypeptide was loaded onto the SEC column at a flow rate of 0.5 ml/min.

For a determination of the apparent molecular weight of the CD95R fusion proteins under native conditions, the Superdex 200 column was calibrated with standard proteins having a known molecular weight. Based on the elution volume of the standard proteins, the apparent molecular weights of the CD95R fusion proteins could be determined.

FIGS. 3A, B, C and D show the elution profiles of SEC chromatograms for the fusion proteins HS95R-A69St (FIG. 3A), HS95R-AT4-St (FIG. 3B), HS95R-ASPD-St (FIG. 3C) and APG101 (FIG. 3D). The individual SEC-runs were performed in different setups with respect to sample amount, loop-volume and calibration. The apparent molecular weight for HS95R-A69St (FIG. 3A) was estimated to be 258 kD; the apparent molecular weight for HS95R-AT4-St (FIG. 3B) was estimated to be 267 kD; the apparent molecular weight for HS95R-ASPD-St (FIG. 3C) was estimated to be 276 kD; and the apparent molecular weight of APG101 (dimeric CD95R-Fc-fusion protein) was estimated to be 240 kDA (FIG. 3D). Taken together with the crosslinking experiments shown in FIGS. 5A, B and C, the data indicates, that the fusion proteins are present as glycosylated, well defined trimeric complexes.

FIGS. 4A, B, C and D show the results of an SDS-PAGE analysis of the SEC fractions of the trimeric CD95-R fusion proteins HS95R-A69-St (FIG. 4A), HS95R-AT4-St (FIG. 4B) and HS95R-ASPD-St (FIG. 4C) as well as the results of the dimeric CD95R-Fc fusion protein (APG101; FIG. 4D) under non-reducing conditions (silver-stain).

The trimeric status of the fusion proteins was analysed by covalent crosslinking studies. A constant amount of the proteins to be analysed (200 ng) was incubated for 30 min at room temperature with increasing amounts of bis(sulfosuccinimidyl) suberate ($BS^3$), a bifunctional cross-linking reagent. Reactions were stopped by the addition of 10 mM Tris/HCl, pH 7.5. Only polypeptide-chains in close proximity to each other are covalently crosslinked.

FIGS. 5A, B and C show a SDS-PAGE analysis of covalently $BS^3$-crosslinked hs95R-A69-St (FIG. 5A), hs95R-AT4-St (FIG. 5B), hs95R-ASPD-St (FIG. 5C) and the dimeric CD95R-Fc fusion protein (APG101, FIG. 5D). The figures show that at low $BS^3$ concentrations, only dimeric and trimeric covalent product formation occurs. At higher $BS^3$ concentrations, the trimeric and multimeric crosslinking products increase.

The anti-apoptotic effect of CD95R fusion proteins was analysed in Jurkat cells. Activation of the CD95R systems in Jurkat cells by extracellular binding of CD95-ligand to the membrane-bound CD95R results in apoptotic cell death. The assay measures an antagonistic effect of the receptor fusion proteins on the pro-apoptotic activity of added recombinant CD95-ligand. As internal control, the dimeric CD95R-Fc fusion protein APG101 was used.

Jurkat cells were grown in flasks with RPMI 1640-medium+GlutaMAX (GibCo) supplemented with 10% FBS, 100 units/ml Penicillin and 100 µg/ml Streptomycin. Prior to the assay, 100,000 cells were seeded per well into a 96-well microtiter plate. The addition of different concentrations of CD95L to the wells was followed by a 3 hour incubation at 37° C. Cells were lysed by adding lysis buffer (250 mM HEPES, 50 mM $MgCl_2$, 10 mM EGTA, 5% Triton-X-100, 100 mM DTT, 10 mM AEBSF, pH 7.5) and plates were put on ice for 30 minutes. Apoptosis is paralleled by an increased activity of Caspase 3 and Caspase 7. Hence, cleavage of the specific Caspase 3/7 substrate Ac-DEVD-AFC (Biomol) was used to determine the extent of apoptosis. In fact, Caspase activity correlates with the percentage of apoptotic cells determined morphologically after staining the cells with propidium iodide and Hoechst-33342. For the Caspase activity assay, 20 µl cell lysate was transferred to a black 96-well microtiterplate. After the addition of 80 µl buffer containing 50 mM HEPES, 1% Sucrose, 0.1% CHAPS, 50 µM Ac-DEVD-AFC, and 25 mM DTT, pH 7.5, the plate was transferred to a Tecan GeniosPro microtiterplate reader and the increase in fluorescence intensity was monitored (excitation wavelength 400 nm, emission wavelength 505 nm).

Prior to the addition of CD95L to the Jurkat cells, a constant amount of CD95L was incubated for 30 min at 37° C. with different concentrations of the comparative dimeric fusion protein CD95R-Fc and the inventive trimeric fusion proteins. The results are shown in the following Table 1:

TABLE 1

| $EC_{50}$ values for multimeric CD95R fusion proteins | |
|---|---|
| $EC_{50}$ | ng/mL |
| APG101 | 594.5 |
| hs95R-AT4-St | 92.6 |
| hs95R-A69-St | 87.6 |
| hs95R-ASPD-St | 573.3 |

It can be seen that the inventive trimeric proteins have a lower EC50 value indicating a higher anti-apoptotic potency compared to APG 101.

The invention claimed is:

1. A fusion protein comprising
   (i) a TNF-family receptor extracellular domain,
   (ii) a flexible linker element comprising more than 2 amino acids between components (i) and (iii), and
   (iii) a collectin trimerization domain comprising a neck and a carbohydrate binding domain.

2. The fusion protein of claim 1 wherein the TNF-family receptor is TNFRSF6 (SEQ ID NO: 6).

3. The fusion protein of claim 2 wherein component (i) comprises amino acids 1 to 169 of TNFRSF6 (SEQ ID NO: 6).

4. The fusion protein of claim 1 wherein component (ii) has a length of from 2-20 amino acids.

5. The fusion protein of claim 4 wherein component (ii) is a glycine/serine linker.

6. The fusion protein of claim 5 wherein component (ii) has the amino acid sequence $(GSS)_a (GSG)_b$ (SEQ ID NO: 41) or $(GTT)_a (GTG)_b$ (SEQ ID NO: 42) wherein a or b is 0, 1, 2, 3, 4 or 5, wherein when a=0 then b is ≥1 and when b=0 then a is ≥1.

7. The fusion protein of claim 1 wherein the collectin is surfactant protein-D, surfactant protein-A, mannan-binding protein-A, mannan-binding-protein-C, collectin liver 1, collectin placenta 1, or collectin-11.

8. The fusion protein of claim 7 wherein component (iii) comprises amino acids 217-375, 218-375, 219-375, 220-375, 221-375, 222-375, 223-375, 224-375, 225-375 of human surfactant protein-D of SEQ ID NO: 59.

9. The fusion protein of claim 1 wherein the collectin comprises only one amino acid substitution of SEQ ID NO: 59 or 60.

10. The fusion protein of claim 9 wherein the amino acid substitution affects amino acid position F355 of human surfactant protein-D of SEQ ID NO: 59.

11. The fusion protein of claim 10 wherein the amino acid substitution is one of the following: F355A, F355S, F355T, F355E, F355D, F355K, or F355R.

12. The fusion protein of claim 9 wherein the collectin is a mutant which does not bind to mannose.

13. The fusion protein of claim 1 wherein component (iii) comprises amino acids 110-271, 116-271, or 121-271 of human collectin-11 of SEQ ID NO: 60.

14. The fusion protein of claim 1 wherein component (i) is located N-terminally and component (iii) is located C-terminally.

15. The fusion protein of claim 1 wherein component (iii) is located N-terminally and component (i) is located C-terminally.

16. The fusion protein of claim 1 which additionally comprises an N-terminal signal peptide domain, which optionally comprises a protease cleavage site.

17. The fusion protein of claim 1 which additionally comprises a C-terminal flexible element which optionally comprises and/or connects to a recognition/purification domain.

18. A trimeric complex consisting of three identical fusion proteins of claim 1.

19. The fusion protein of claim 2 wherein component (i) comprises Arg17-Glu168 of TNFRSF6 (SEQ ID NO: 6).

20. The fusion protein of claim 7 wherein the collectin is collectin-11.

21. An isolated nucleic acid molecule encoding the fusion protein of claim 1, optionally operatively linked to an expression control sequence.

22. An isolated cell transformed or transfected with the nucleic acid molecule of claim 21.

* * * * *